US010883990B2

(12) United States Patent
Lalvani et al.

(10) Patent No.: US 10,883,990 B2
(45) Date of Patent: Jan. 5, 2021

(54) METHODS AND KITS FOR DETERMINING TUBERCULOSIS INFECTION STATUS

(71) Applicant: MJO Innovations Limited, London (GB)

(72) Inventors: Ajit Lalvani, Oxford (GB); Katrina Mary Pollock, London (GB); Graham Taylor, London (GB); Hilary Sian Whitworth, London (GB)

(73) Assignee: MJO INNOVATION LIMITED, London (GB)

( * ) Notice: Subject to any disclaimer, the term of this patent is extended or adjusted under 35 U.S.C. 154(b) by 0 days.

(21) Appl. No.: 16/026,523

(22) Filed: Jul. 3, 2018

(65) Prior Publication Data

US 2018/0313835 A1 Nov. 1, 2018

Related U.S. Application Data

(63) Continuation of application No. 14/916,632, filed as application No. PCT/GB2014/052667 on Sep. 4, 2014, now Pat. No. 10,041,944.

(30) Foreign Application Priority Data

Sep. 4, 2013 (GB) .................................. 1315748.2

(51) Int. Cl.
*A61K 39/00* (2006.01)
*A61K 39/04* (2006.01)
*G01N 33/00* (2006.01)
*G01N 33/569* (2006.01)
*G01N 33/50* (2006.01)

(52) U.S. Cl.
CPC ..... *G01N 33/56966* (2013.01); *G01N 33/505* (2013.01); *G01N 33/5695* (2013.01); *A61K 39/04* (2013.01); *G01N 2333/35* (2013.01); *G01N 2333/525* (2013.01); *G01N 2333/57* (2013.01); *G01N 2333/70514* (2013.01); *G01N 2333/70517* (2013.01); *G01N 2333/70589* (2013.01); *G01N 2800/26* (2013.01); *G01N 2800/56* (2013.01)

(58) Field of Classification Search
CPC ........ A61K 39/00; A61K 39/02; A61K 39/04; G01N 33/00; G01N 33/33; G01N 33/53
USPC ...... 424/130.1, 234.1, 248.1; 435/4, 7.1, 7.2
See application file for complete search history.

(56) References Cited

U.S. PATENT DOCUMENTS

| 7,364,869 B2 | 4/2008 | Nixon et al. |
| 7,785,607 B2 | 6/2010 | Goletti et al. |
| 10,041,944 B2 * | 8/2018 | Lalvani ................ G01N 33/505 |
| 2009/0011426 A1 | 1/2009 | Mackintosh et al. |
| 2009/0068197 A1 | 3/2009 | Steyn et al. |
| 2010/0267009 A1 | 10/2010 | Schollhorn |
| 2010/0279324 A1 | 11/2010 | Lalvani et al. |
| 2011/0021367 A1 | 1/2011 | Gopal |
| 2011/0070599 A1 | 3/2011 | Park et al. |
| 2011/0129817 A1 | 6/2011 | Banchereau et al. |
| 2011/0196614 A1 | 8/2011 | Banchereau et al. |
| 2011/0236411 A1 | 9/2011 | Scholler et al. |
| 2011/0268744 A1 | 11/2011 | Garthwaite et al. |

FOREIGN PATENT DOCUMENTS

| WO | 2007014304 | 2/2007 |
| WO | 2007107714 | 9/2007 |
| WO | 2009158521 | 12/2009 |
| WO | 2010070581 | 6/2010 |
| WO | 2010149657 | 12/2010 |
| WO | 2011044508 | 4/2011 |
| WO | 2011113953 | 9/2011 |
| WO | 2012085652 | 6/2012 |
| WO | 2013113092 | 8/2013 |
| WO | 2014039044 | 3/2014 |

OTHER PUBLICATIONS

Berry et al. (2010). An interferon-inducible neutrophil-driven blood transcriptional signature in human tuberculosis. Nature. 466(7309):973-7.
Caccamo et al. (2009). "Analysis of *Mycobacterium tuberculosis*-specific CD8 T-cells in patients with active tuberculosis and in individuals with latent infection." PLoS One 4(5): e5528.
Caccamo et al. (2010). Multifunctional CD4(+) T cells correlate with active *Mycobacterium tuberculosis* infection. Eur J Immunol. 40(8):2211-20.
Casey et al. (2010). "Enumeration of functional T-cell subsets by fluorescence-immunospot defines signatures of pathogen burden in tuberculosis." PLoS One 5(12): e15619.
Chapman et al. (2002). "Rapid detection of active and latent tuberculosis infection in HIV-positive individuals by enumeration of *Mycobacterium tuberculosis*-specific T cells." AIDS 16(17): 2285-2293.
Cobelens et al. (2006). "Tuberculin skin testing in patients with HIV infection: Limited benefit of reduced cutoff values." Clinical Infectious Diseases 43(5): 634-639.
Cote et al. (1983). Generation of human monoclonal antibodies reactive with cellular antigens. Proc Natl Acad Sci U S A. 80(7):2026-30.

(Continued)

*Primary Examiner* — Rodney P Swartz
(74) *Attorney, Agent, or Firm* — Robert C. Netter, Jr.; Dann, Dorfman, Herrell & Skillman

(57) ABSTRACT

There is provided methods of determining tuberculosis (TB) infection status in an individual comprising: (i) providing a sample comprising T-cells; (ii) exposing the sample of (i) to one or more TB antigens; (iii) identifying T-cells in the sample that are CD4 positive and (a) secrete TNF-α without secreting IFN-γ; or (b) secrete IFN-γ without secreting TNF-α; (iv) identifying those cells of (iii) which are also CCR7 and, CD127 negative; and optionally (v) calculating the cells identified in (iv) as a percentage of those identified in (iii); wherein the identification of cells in (iv) and/or the percentage of T-cells calculated in (v) correlates to TB infection status of the individual, and wherein steps (iii) and (iv) can be carried out either sequentially or simultaneously. There are also provided compositions and kits for use in such methods.

11 Claims, 23 Drawing Sheets

(56) References Cited

OTHER PUBLICATIONS

Cole et al. (1984). Human monoclonal antibodies. Mol Cell Biochem. 62(2):109-20.
Crawley and Angel (2012). "Expression of gamma-chain cytokine receptors on CD8(+) T cells in HIV infection with a focus on IL-7Ralpha (CD127)", Immunol Cell Biol 90(4):379-87. Epub Aug. 23, 2011.
Day et al. (2011). Functional capacity of *Mycobacterium tuberculosis*-specific T cell responses in humans is associated with mycobacterial load. J Immunol. 187(5):2222-32. Epub Jul. 20, 2011.
Dessein et al. (2013). Heparin-binding haemagglutinin, a new tool for the detection of latent *Mycobacterium tuberculosis* infection in hemodialysis patients. PLoS One. Aug. 5, 2013;8(8):e71088.
Diel et al. (2011). "Interferon-gamma release assays for the diagnosis of latent *Mycobacterium tuberculosis* infection: a systematic review and meta-analysis." Eur Respir J 37(1): 88-99.
Dinnes et al. (2007). "A systematic review of rapid diagnostic tests for the detection of tuberculosis infection." Health technology assessment 11(3): 1-196.
Dosanjh et al. (2011). "Novel *M tuberculosis* antigen-specific T-cells are early markers of infection and disease progression." PLoS One 6(12): e28754.
Dosanjh et al. (2008). "Improved diagnostic evaluation of suspected tuberculosis." Ann Intern Med 148(5): 325-336.
Dunham et al. (2008). CD127 and CD25 expression defines CD4+ T cell subsets that are differentially depleted during HIV infection. J Immunol. 180(8):5582-92.
Goletti et al. (2006). "Region of difference 1 antigen-specific CD4+ memory T cells correlate with a favorable outcome of tuberculosis." J Infect Dis 194(7): 984-992.
Harari et al. (2004). "Skewed representation of functionally distinct populations of virus-specific CD4 T cells in HIV-1-infected subjects with progressive disease: changes after antiretroviral therapy." Blood 103(3): 966-972.
Harlow & Lane (1988). Antibodies: A Laboratory Manual. Cold Spring Harbor Laboratory, New York.
Harrington et al. (2008). Memory CD4 T cells emerge from effector T-cell progenitors. Nature. 452(7185):356-60. Epub Mar. 5, 2008.
Hurrell (1982). Monoclonal Hybridoma Antibodies: Techniques and Applications. CRC Press.
Harari et al. (2011) "Dominant TNF-alpha+ *Mycobacterium tuberculosis*-specific CD4+ T cell responses discriminate between latent infection and active disease." Nat Med 17(3): 372-376.
HPA (2011). "Tuberculosis in the UK." Retrieved Dec. 2011, from http://www.hpa.org.uk/webc/HPAwebFile/HPAweb_C/ 1317131791612.
Kaech et al. (2003). Selective expression of the interleukin 7 receptor identifies effector CD8 T cells that give rise to long-lived memory cells. Nat Immunol. 4(12):1191-8. Epub Nov. 16, 2003.
Kassa et al. (2012). Analysis of immune responses against a wide range of *Mycobacterium tuberculosis* antigens in patients with active pulmonary tuberculosis. Clin Vaccine Immunol. 19(12)1907-15. Epub Sep. 26, 2012.
Köhler and Milstein (1975). Continuous cultures of fused cells secreting antibody of predefined specificity. Nature. 256 (5517):495-7.
Kozbor et al. (1985). Specific immunoglobulin production and enhanced tumorigenicity following ascites growth of human hybridomas. J Immunol Methods. 81(1):31-42.
Millington et al. (2007). "Dynamic relationship between IFN-gamma and IL-2 profile of *Mycobacterium tuberculosis*-specific T cells and antigen load." J Immunol 178(8): 5217-5226.
Mueller et al. (2008). "*Mycobacterium tuberculosis*-specific CD4+, IFNgamma+, and TNFalpha+ multifunctional memory T cells coexpress GM-CSF." Cytokine 43(2): 143-148.
Orlandi et al. (1989). Cloning immunoglobulin variable domains for expression by the polymerase chain reaction. Proc Natl Acad Sci U S A. 86(10):3833-7.
Pedersen et al. (2011). Pandemic influenza vaccination elicits influenza-specific CD4+ Th1-cell responses in hypogammaglobulinaemic patients: four case reports. Scand J Immunol. 74(2):210-8.
Pollock et al. (2013). T-cell immunophenotyping distinguishes active from latent tuberculosis. J Infect Dis. 208 (6):952-68.
Pollock et al. (2011). S43 Polyfunctional T cells reveal the spectrum of tuberculosis in HIV co-infection through the identification of immunological correlates of latent and active disease. Thorax 66:A22-A23. British Thoracic Society winter meeting, oral presentation (abstract).
Schluns et al. (2003). Cytokine control of memory T-cell development and survival. Nat Rev Immunol. 3(4):269-79.
Streitz et al. (2012). The phenotypic distribution and functional profile of tuberculin-specific CD4 T-cells characterizes different stages of TB infection. Cytometry B Clin Cytom. 82(6):360-8. Epub Sep. 2012.
Tena-Coki et al. (2010). CD4 and CD8 T-cell responses to mycobacterial antigens in African children. Am J Respir Crit Care Med. 182(1):120-9. Epub Mar. 11, 2010.
Wang et al. (2010). "Association of mycobacterial antigen-specific CD4(+) memory T cell subsets with outcome of pulmonary tuberculosis." The Journal of infection 60(2): 133-139.
Whitworth et al. (2013). Biomarkers of tuberculosis: a research roadmap. Biomark Med. 7(3):349-62.
Winter and Milstein (1991). Man-made antibodies. Nature. 349(6307):293-9.
WHO (2011). "TB/HIV facts" Retrieved Dec. 2011, 2011, from http://www.who.int/tb/challenges/hiv/factsheet_hivtb_2011.pdf.
Zola (1988). Monoclonal Antibodies: A manual of techniques. CRC Press.
International Search Report and Written Opinion of the International Searching Authority in PCT/GB2014/052667, dated Feb. 12, 2015.

\* cited by examiner

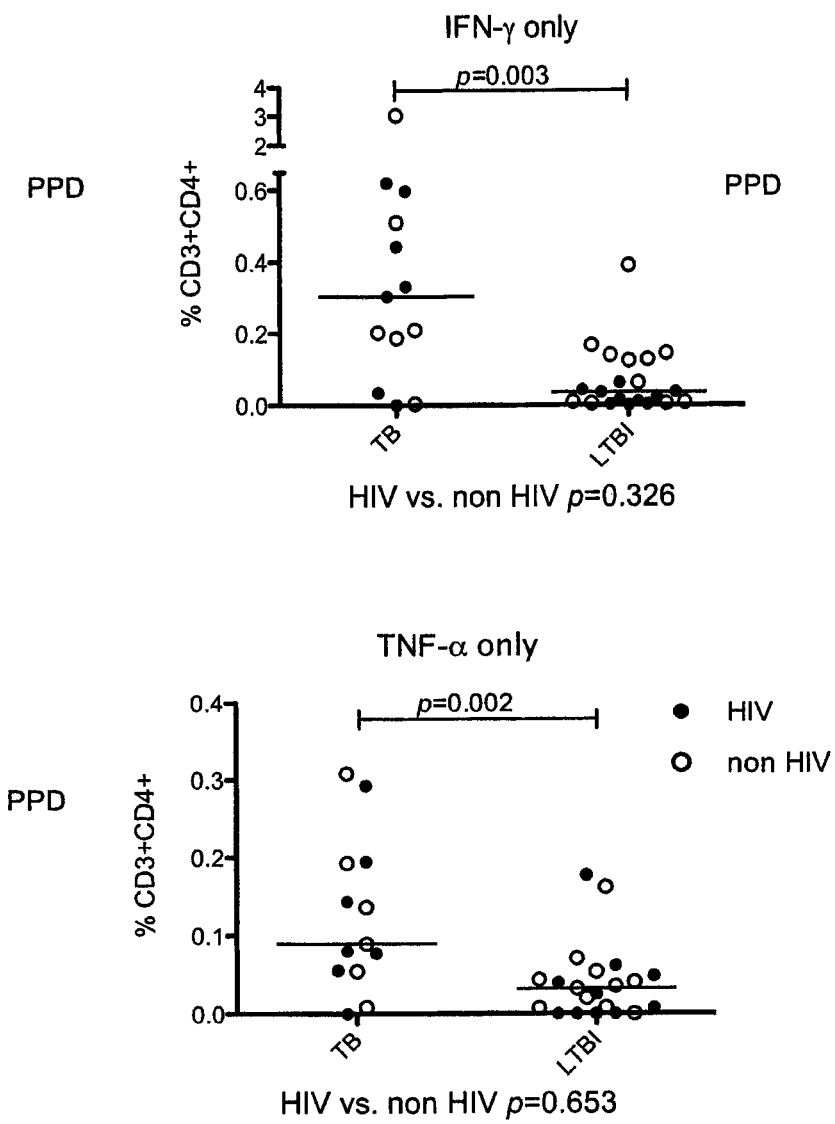
Figure 1 (con't)

B(con't)
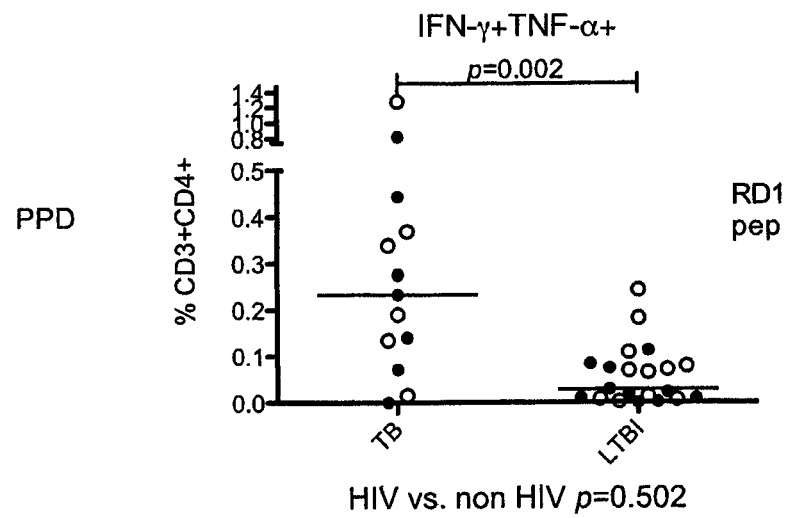
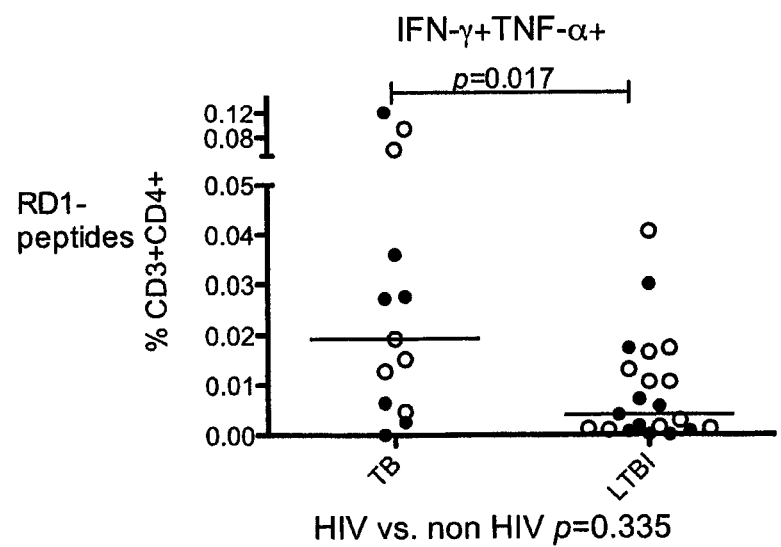
Figure 1 (con't)

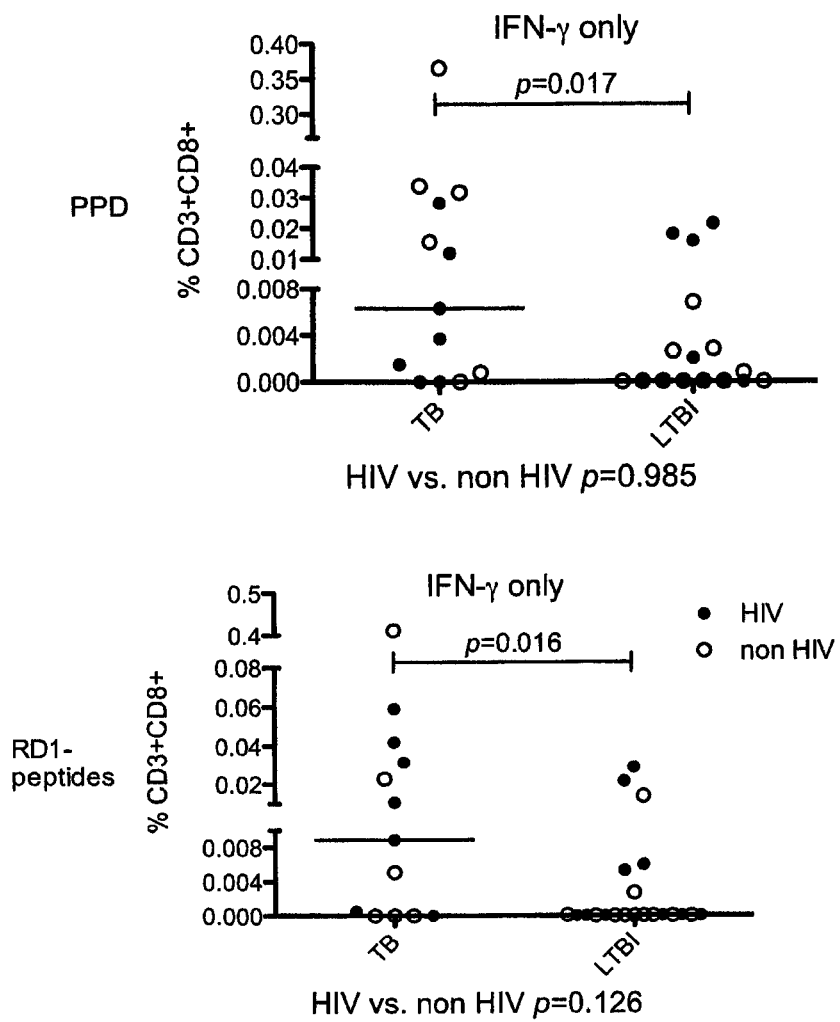
Figure 1 (con't)

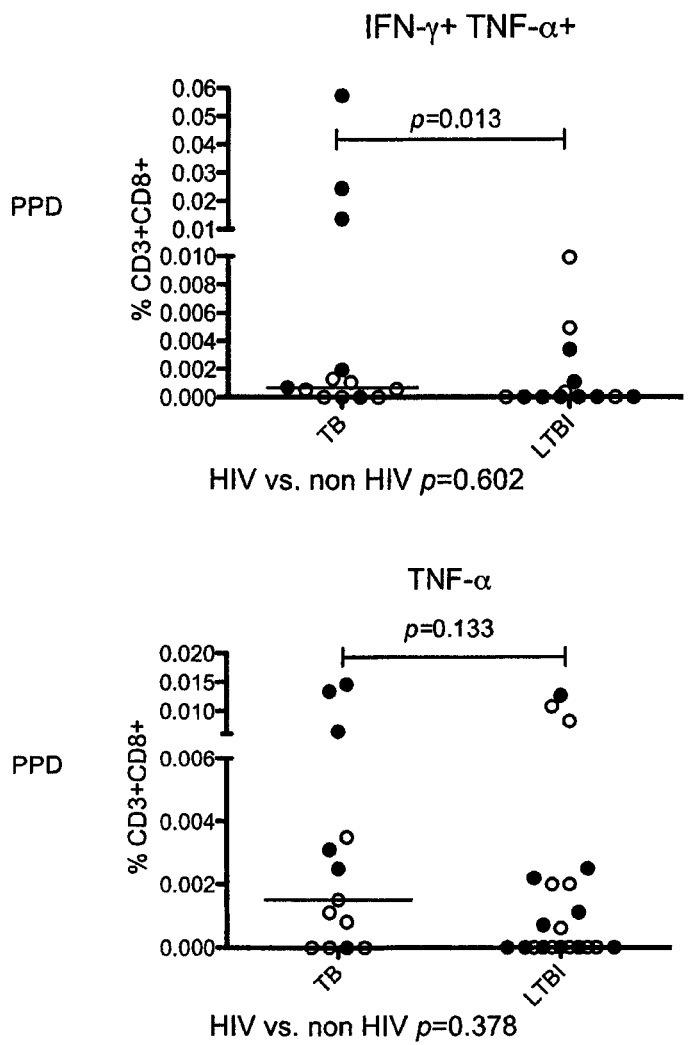
Figure 1 (con't)

B
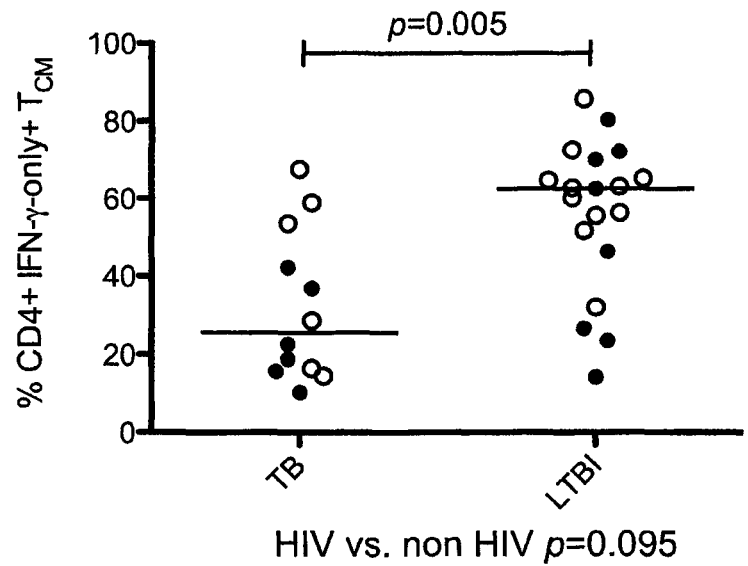
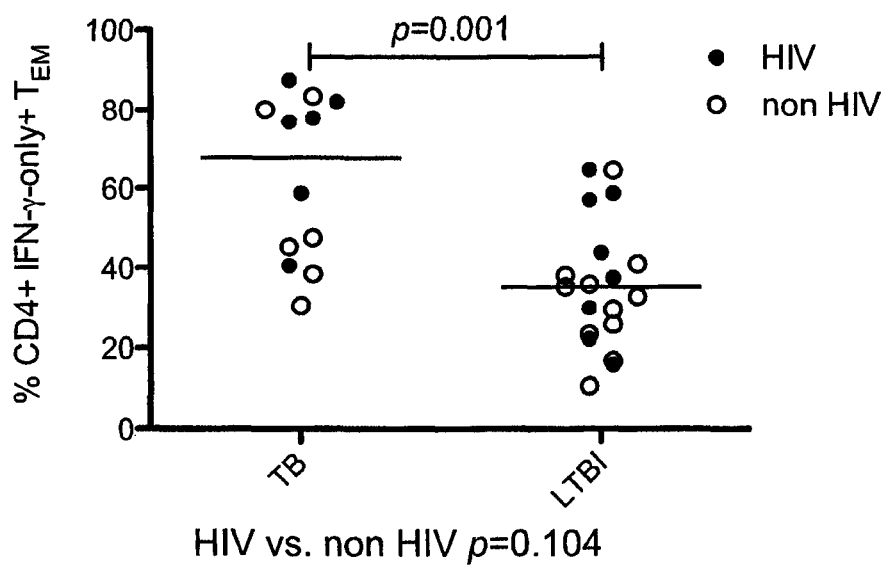
Figure 2 (con't)

B (con't)
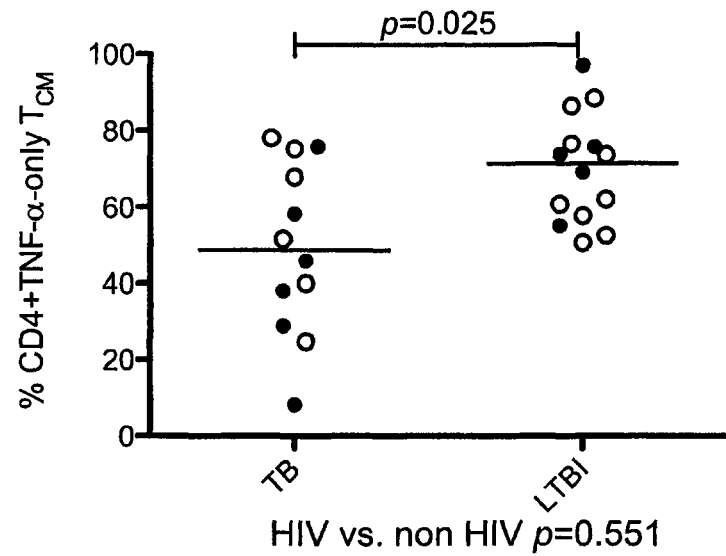
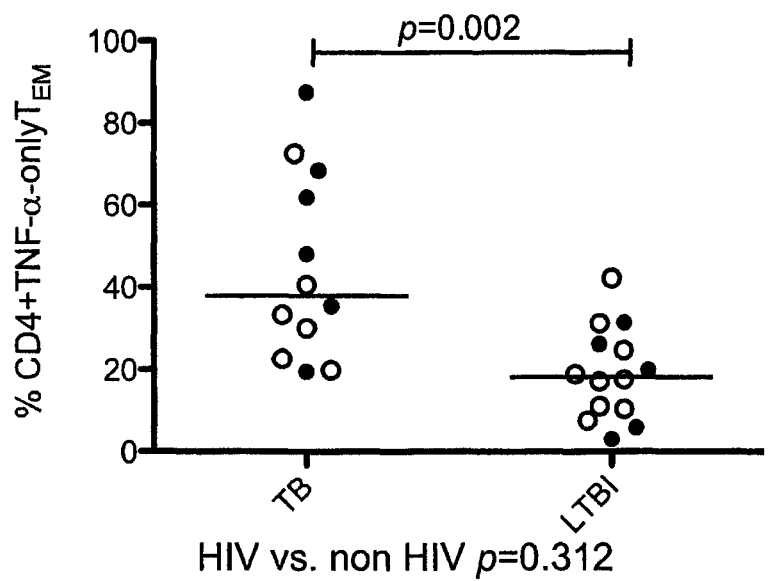
Figure 2 (con't)

B (con't)
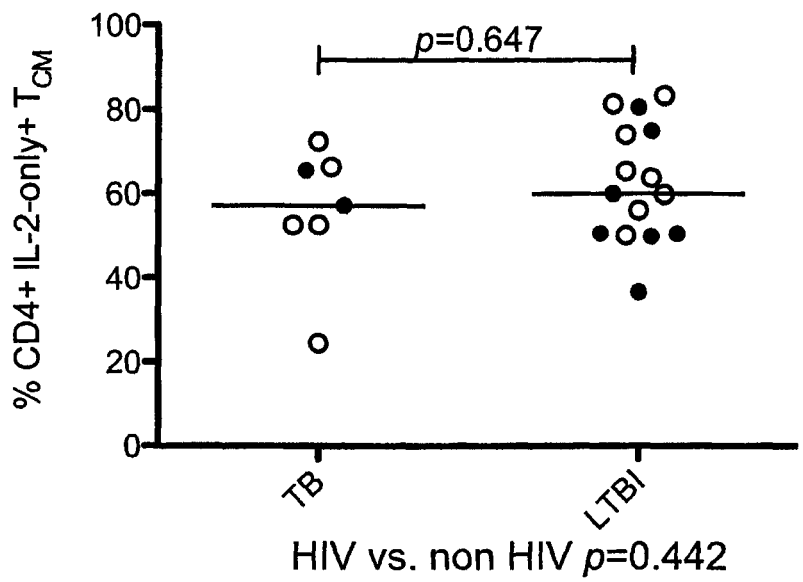
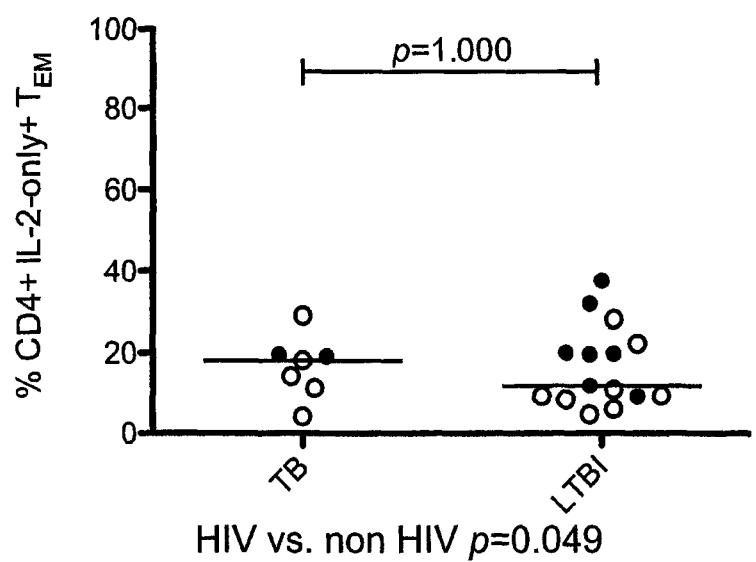
Figure 2 (con't)

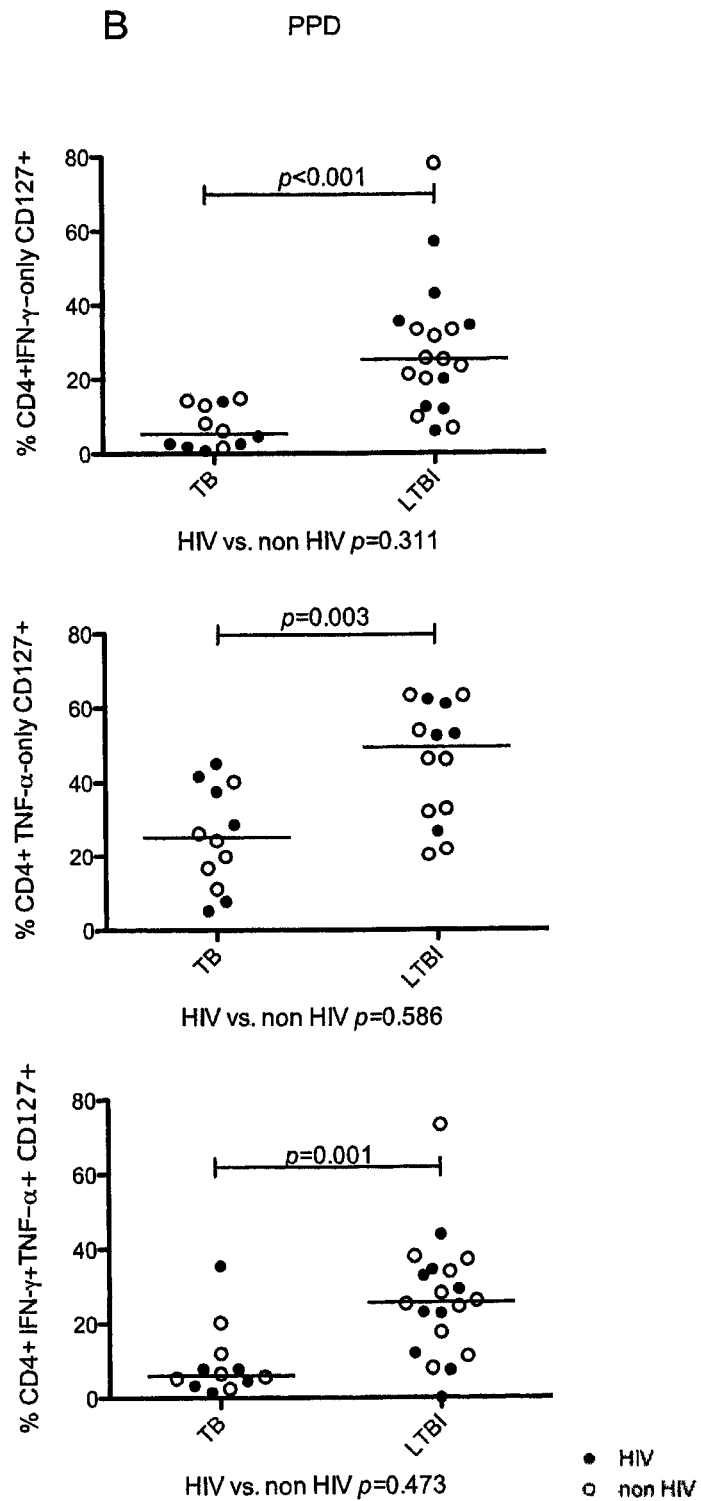
Figure 3 (con't)

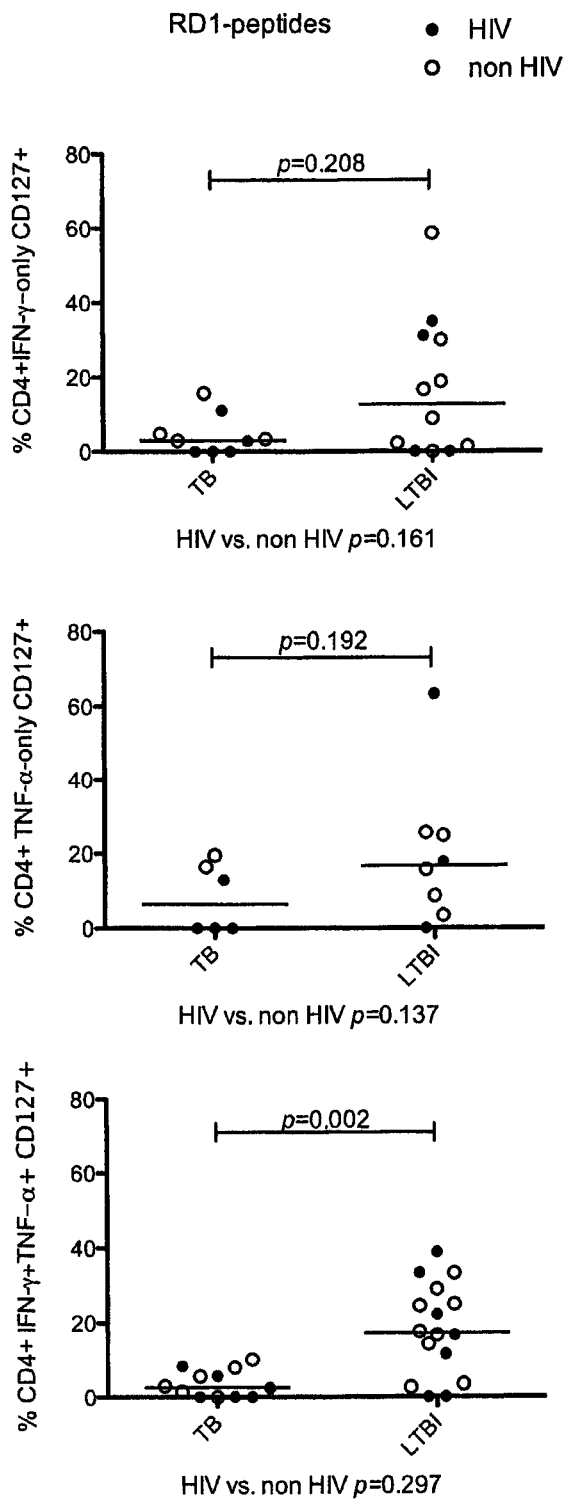
*Figure 3 (con't)*

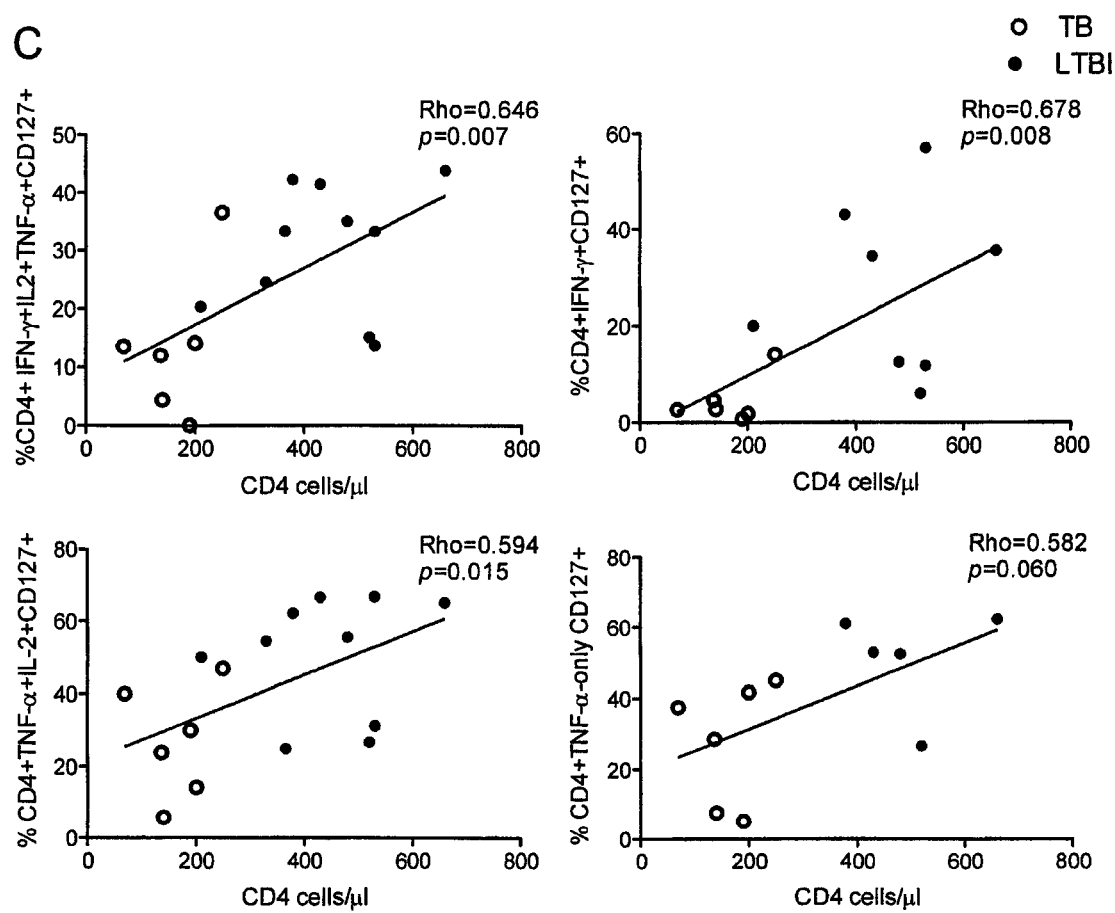
Figure 3 (con't)

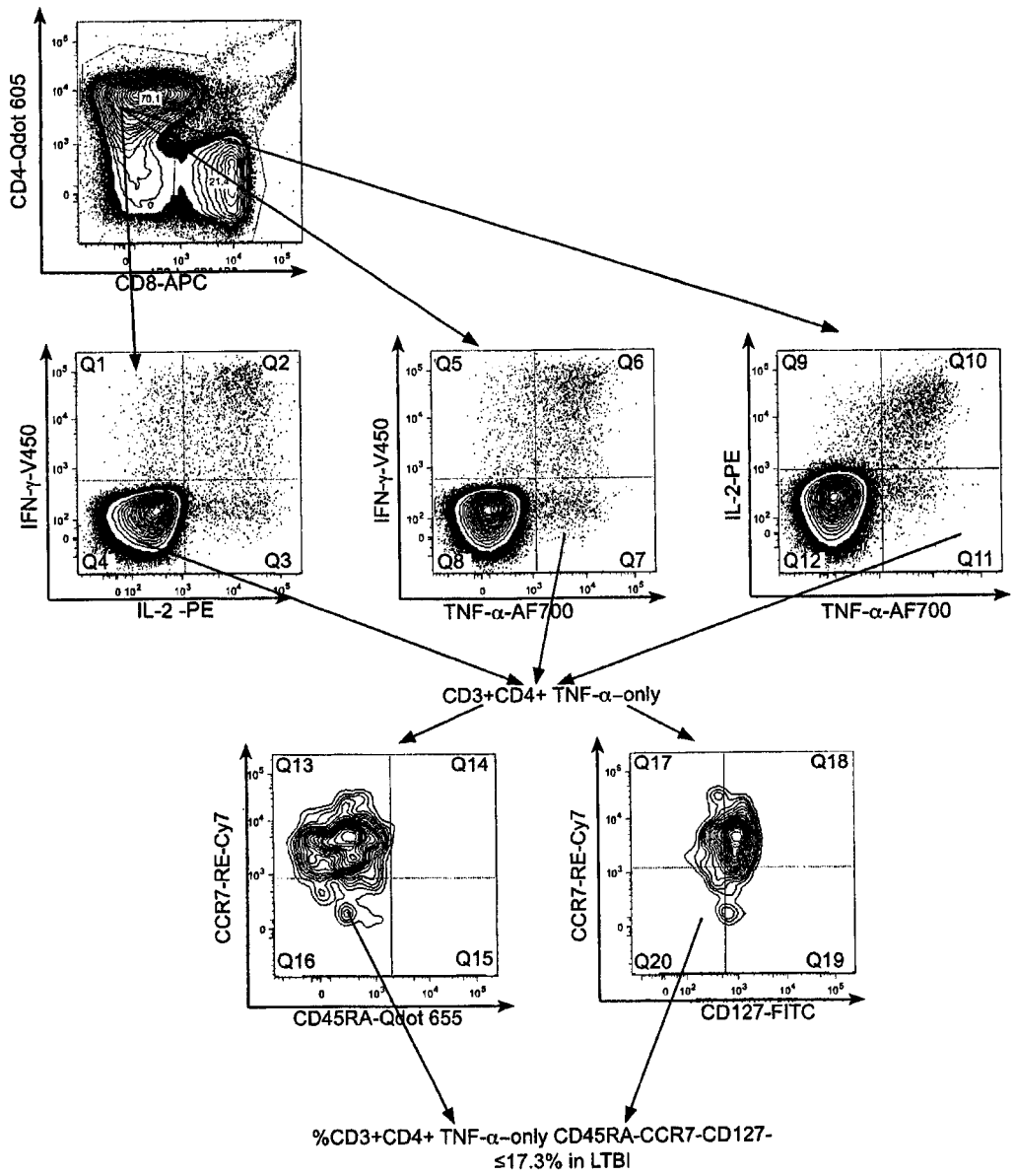
Figure 4 (con't)

C
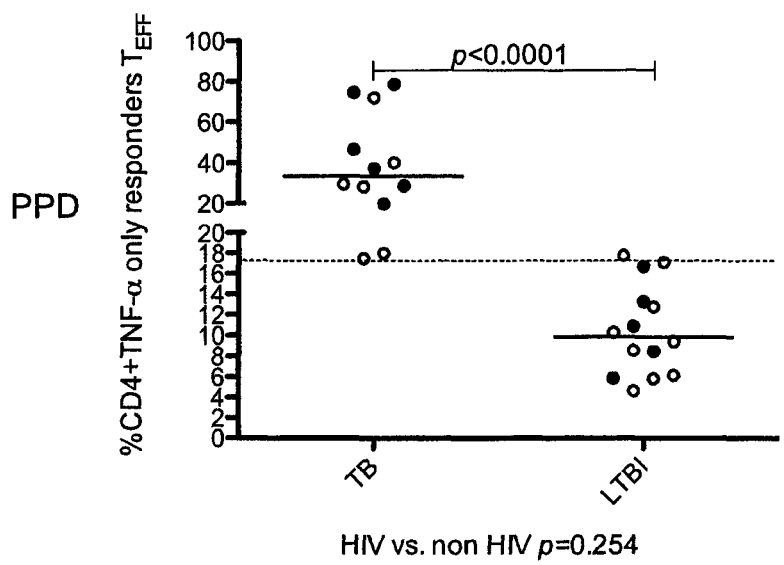
- HIV
- non HIV
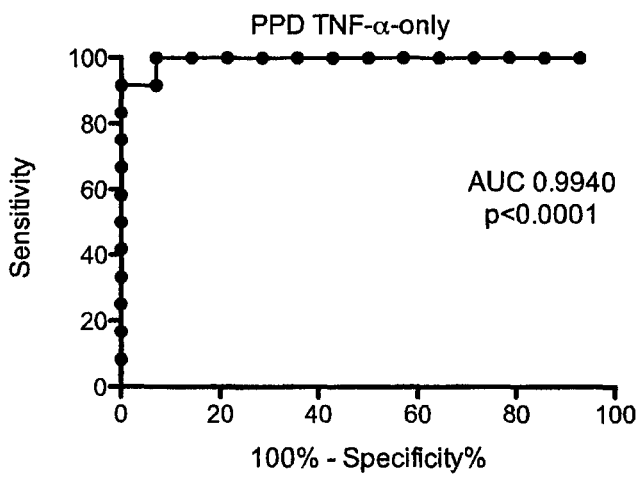
Figure 4 (con't)

C (con't)
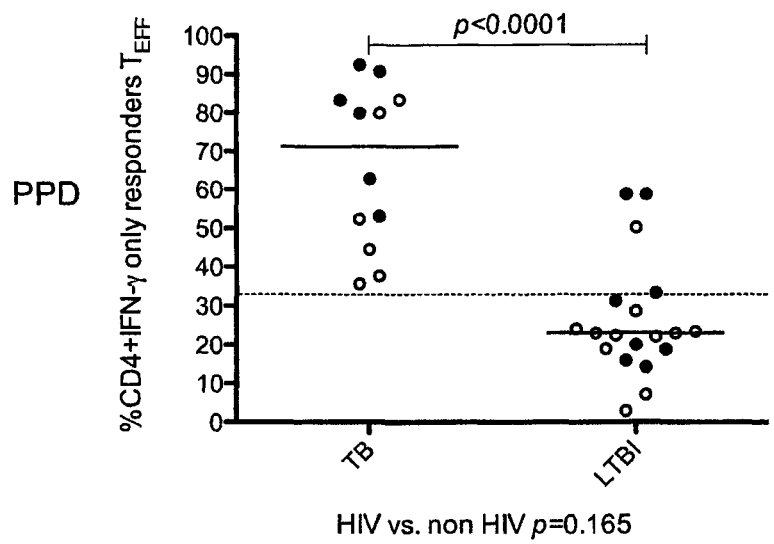
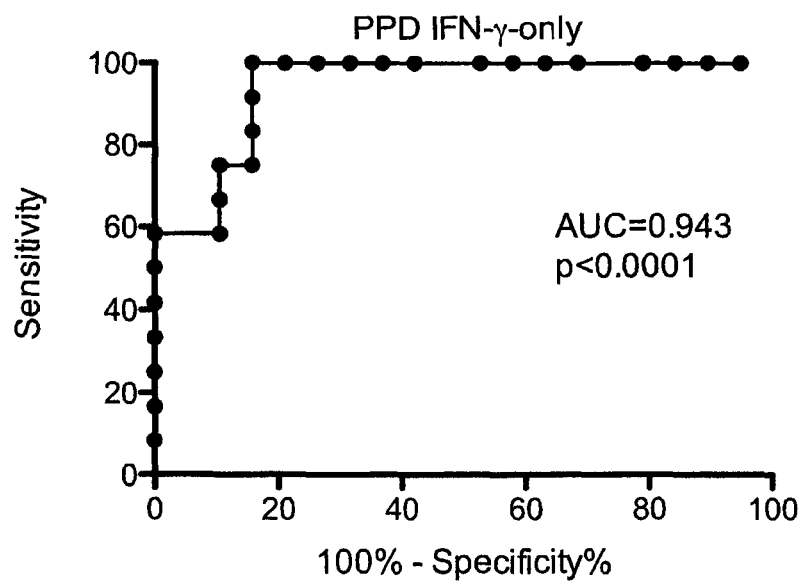
Figure 4 (con't)

C (con't)
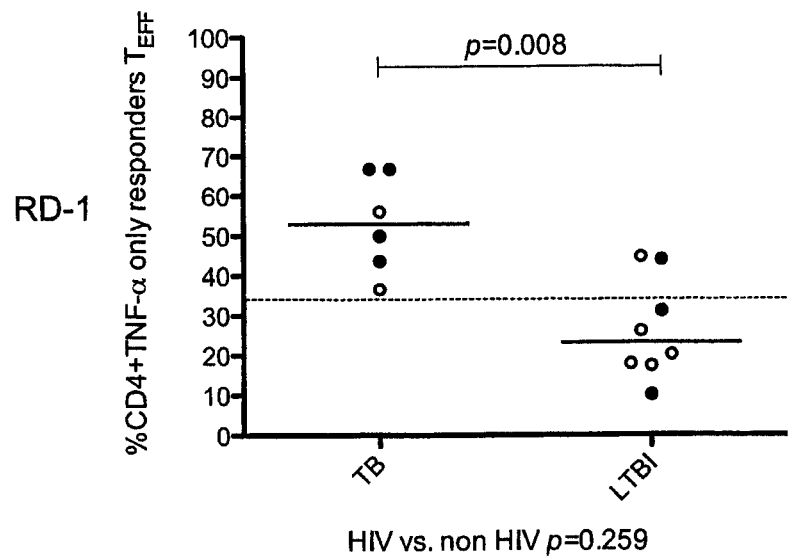
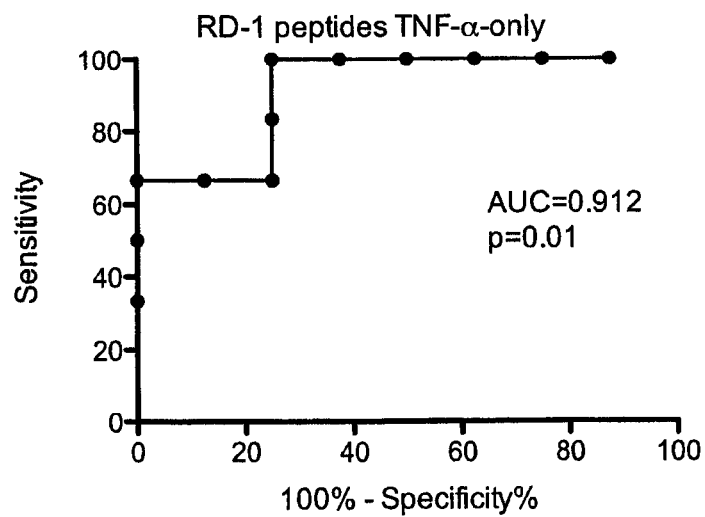
Figure 4 (con't)

C (con't)
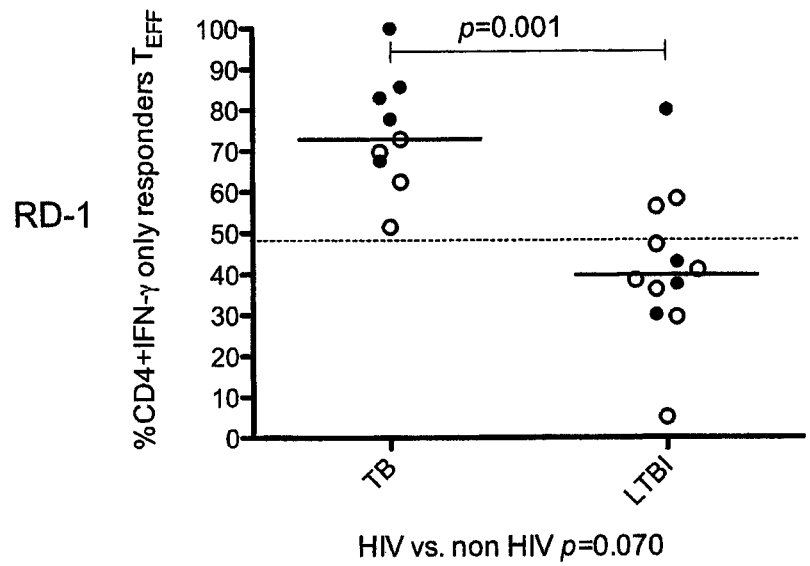
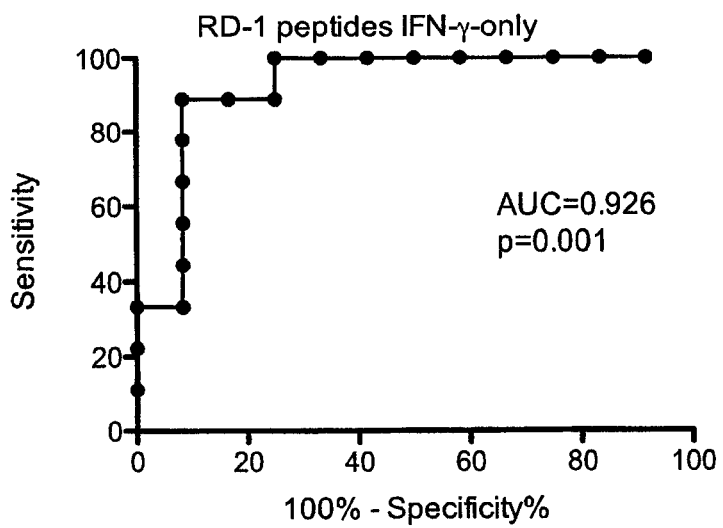
Figure 4 (con't)

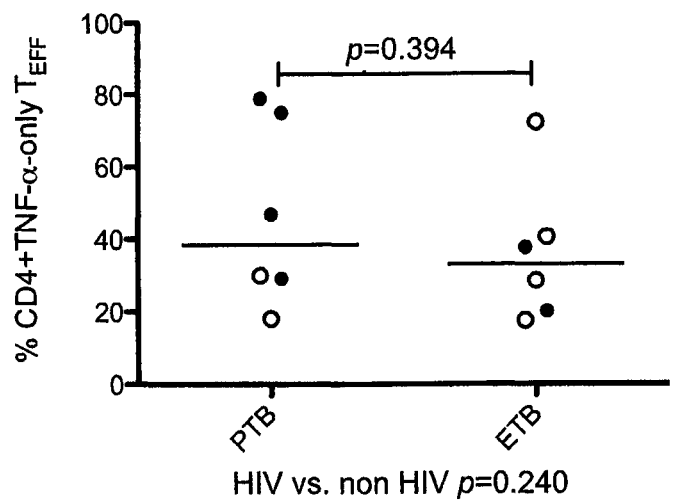
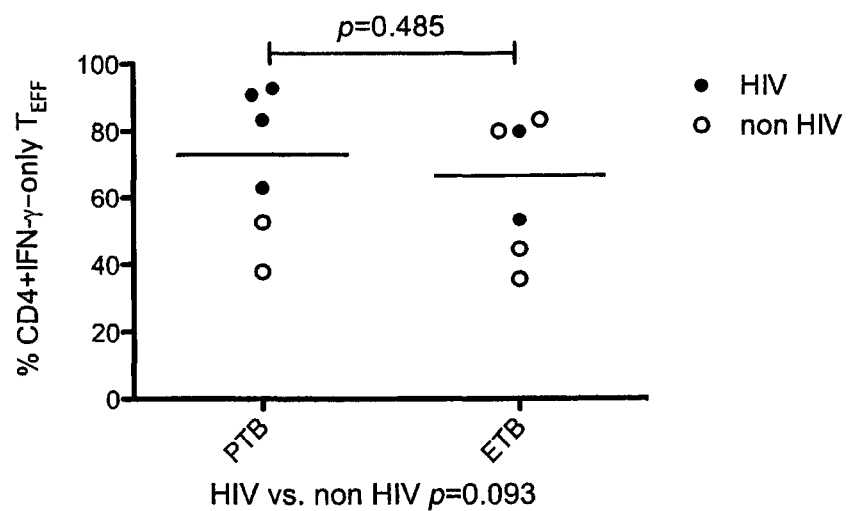
Figure 4 (con't)

(a)

(b)

METHODS AND KITS FOR DETERMINING TUBERCULOSIS INFECTION STATUS

This application is a continuation of U.S. patent application Ser. No. 14/916,632, filed Mar. 4, 2016, now U.S. Pat. No. 10,041,944, which is a § 371 application of International Application No. PCT/GB2014/052667, filed Sep. 4, 2014, which claims priority from Great Britain Patent Application No. 1315748.2, filed Sep. 4, 2013. The entire disclosure of each of the aforesaid applications is incorporated by reference in the present application.

The present invention relates to methods for determining tuberculosis infection status and compositions and kits for use in such methods.

Worldwide there are almost 2 million deaths due to active tuberculosis (TB) every year (World Health Organisation (WHO) 2011) and in the developed world, including the UK, rates of TB have risen (Health Protection Agency (HPA) 2011).

Clinicians treating TB face two major challenges:
1) Diagnostic distinction of active TB and latent TB infection ("ATB" and "LTBI", respectively)
2) Prioritising treatment of LTBI to those most likely to progress to active TB.

Unlike, for example HIV infection, where the amount of virus in the body (plasma or other compartments) is directly quantifiable using PCR, there is no comparable test to directly measure mycobacterial (e.g. *Mycobacterium tuberculosis*) pathogen load. A widely used TB diagnostic assay, the mantoux or tuberculin skin test (TST), uses an immune-based approach to demonstrate the presence of infection with *Mycobacterium tuberculosis* (MTB). The TST has poor specificity especially in those who are BCG-vaccinated (Diel, Goletti et al. 2011) and poor sensitivity especially in those who are immunocompromised e.g. with HIV infection (Cobelens, Egwaga et al. 2006).

The recently introduced interferon-gamma release assays (IGRAs) also use an immune-based approach, which is more quantifiable than the mantoux test and less open to confounding by BCG vaccination or exposure to environmental mycobacteria. Neither the mantoux test nor the IGRAs nor indeed any other commercially available assay can reliably distinguish between latent, active or treated TB or predict which patients with LTBI are likely to progress to active TB.

Approximately half of pulmonary TB cases are smear positive for acid fast bacilli (HPA 2011). This method for diagnosing active TB is therefore not very sensitive and is highly disease site specific. The gold standard diagnostic test for active TB is microbiological culture. This was only positive in 58% of cases reported in the UK in 2010 (HPA 2011) and is especially difficult to interpret in paucibacillary disease e.g. lymph node TB, central nervous system TB (CNS TB) and in HIV co-infection. This method of diagnosis is also confined to accessing the site of disease, which can be challenging. The new PCR based approaches e.g. GeneXpert, whilst quicker than microbiological culture cannot distinguish active from latent TB. Both CNS TB and TB with HIV co-infection are associated with high morbidity and mortality. Early and accurate diagnosis is therefore of paramount importance.

Investigation of both active and latent TB infection may involve multiple invasive, time consuming and expensive tests such as CT with contrast, bronchoscopy, biopsy or PET scanning. A blood test that could reduce the need for such intensive investigation would therefore be of great benefit to both patients and healthcare providers.

Treatment of active TB requires a longer, more complex and more toxic treatment regime than the chemoprophylaxis used for LTBI, however both can be associated with potentially life-threatening toxicity. Many therapeutics currently used to treat mycobacterial infection have high associated morbidity e.g. peripheral neuropathy and mortality e.g. liver necrosis. Therefore use of the appropriate shortest and most effective therapeutic regime is vital.

Misdiagnosis of active TB as LTBI can lead to uncontrolled mycobacterial replication and increases the risk of drug resistance, which is more difficult to treat and has a higher associated morbidity and mortality. Misdiagnosis of LTBI and consequent treatment as active TB exposes patients to unnecessary and sometimes toxic therapies for a prolonged period. Furthermore, as most patients with LTBI will never progress to active TB, there is therefore an opportunity to improve care by identifying those most likely to progress and prioritising them to receive treatment. Those unlikely to progress would thus be able to avoid taking chemoprophylaxis altogether.

Currently there is no diagnostic test able to distinguish these two groups. However, given that the likelihood of progression is greatest in the first 2-3 years following MTB infection, correlates of time since exposure may provide a means for risk stratification.

Some data have shown that changes in the antigen-specific cellular immune response mirror pathogen burden and clearance e.g. in cytomegalovirus and HIV infections (Harari, Petitpierre et al. 2004). Recent work on the MTB-specific cellular immune response has suggested that this paradigm holds true in TB (Casey, Blumenkrantz et al.; Millington, Innes et al. 2007). Further studies have focused on using either MTB-specific cell function or cell phenotype to try to distinguish between active and latent infection (Harari, Rozot et al.; Goletti, Butera et al. 2006; Wang, Cao et al. 2010; Mueller, Detjen et al. 2008; Caccamo, Guggino et al. 2009).

WO 2007/107714 describes the use of T-cell IFN-γ and IL-2 secretion in assessing the outcome of infections such as TB. WO 2009/158521 describes using differential expression of a large number of genes for distinguishing between active and latent TB. Caccamo et al. (2010) Eur. J. Immunol 40: 2211-2220 describe the use of the T-cell subset that expresses TNF-α, IFN-γ and IL-2 as correlating with active TB. Data in the wider literature on the correlation of multi-functional (and here specifically tri-functional) MTB-specific T-cell frequency with the presence of active TB is both limited and conflicting. WO 2011/044508 describes the use of differential expression of T-cell antigens in the evaluation of prognoses of patients suffering from chronic pulmonary diseases generally. WO 2012/085652 describes the use of CD4 positive T-cells in a method which is 66.67% sensitive and 92.41% specific in the differentiation between active and latent TB infection, based only on the percentage of those cells that produce TNF-α but not IFN-γ or IL-2.

To date, it has not been recognised that loss of CD127 expression can be used to discriminate a subset of differentiated effector T cells or showed clearly that the changes measured in active versus latent TB were independent of HIV co-infection. Therefore, none demonstrated an approach that was sufficiently sensitive or specific enough to be taken forward as a clinical diagnostic test or widely applicable to the HIV co-infected population. Furthermore, these tests were not evaluated with a view to risk stratification in LTBI. In addition, the results from, WO 2012/085652, were not fully replicable from our own data or in other studies comparing active and latent TB e.g. Caccamo et al. (2010) Eur. J. Immunol 40: 2211-2220.

The inventors now combine simultaneous measurement of both cellular phenotype and function to give highly detailed data on the MTB-specific cellular immune response. They have shown for the first time, that when combined, MTB-specific cell phenotype and function are closely linked to TB disease stage e.g. active versus latent and that these changes are independent of HIV co-infection.

The method described herein can distinguish between active and latent TB with a sensitivity of 100%, specificity of 93% and on receiver operator characteristic analysis, the area under the curve of was 0.994 (the value for a perfect test being 1).

Furthermore, this data suggests that, within LTBI, this combined measurement may be a clinically relevant approach to risk stratification by distinguishing individuals who have been recently versus remotely infected. This novel combined approach therefore provides the most accurate proxy of TB disease activity to date.

The inventors now provide the most sensitive and specific immunological approach to date for distinction of active and latent infection and indication of mycobacterial disease activity based on the measurement of the phenotype (CD45RA−CCR7−CD127−) of a specific subset of CD4+ MTB-antigen responsive cells.

Advantages of the method provided by the inventors over the currently used tests can be seen in Table A.

(iv) identifying those cells of (iii) which are also CCR7 and CD127 negative; and optionally
(v) calculating the cells identified in (iv) as a percentage of those identified in (iii);
wherein the identification of cells in (iv) and/or the percentage of cells calculated in (v) correlates to TB infection status of the individual, and wherein steps (iii) and (iv) can be carried out either sequentially or simultaneously.

Steps (i) and (ii) may be performed as a distinct methodology e.g. as part of an alternative assay such as an IGRA (interferon-gamma release assay), ELISpot (Enzyme-Linked Immunosorbent Spot), or TBSpot assay and consequently may be performed at a different time or using a different piece of equipment (e.g. well plate) or even a different physical location to the remaining steps.

In certain embodiments, the cells identified in step (iv) of the methods are additionally CD45RA negative.

In certain embodiments, the cells identified in step (iii) of the methods additionally do not secrete IL-2.

In certain embodiments the cells identified in step (iii) of the methods are additionally CD3 positive.

In certain embodiments the cells identified in step (iii) of the methods are additionally CD8 negative.

"TB" is used interchangeably herein with "MTB" and "tuberculosis". It is intended to include TB caused by any MTB specific causing organisms including *Mycobacterium tuberculosis*, *Mycobacterium bovis* and *Mycobacterium africanum*. It is particularly preferred that the TB is caused by *Mycobacterium tuberculosis*.

TABLE A

Advantages of the methods of the invention over current techniques

| Test | TST | IGRA | Smear | MTB culture | PCR | Radiology (X-ray/CT) | The methods of the Invention |
|---|---|---|---|---|---|---|---|
| Provides evidence of current infection with MTB | Yes | Yes | Yes | Yes | Yes | Yes | Yes |
| Confounded by previous (treated) MTB infection | Yes | Yes/ unknown | No | No | No | Yes | Unknown, probably not |
| Useful to diagnose LTBI | Yes | Yes | No | No | No | Yes | Yes |
| Useful to diagnose active TB | No | Possibly | Yes | Yes | Yes | Yes | Yes |
| Test is dependent on site of TB disease | No | No | Yes | Yes | Yes | Yes | No |
| Confounded by prior BCG vaccination | Yes | No | No | No | No | No | Dependent on antigen |
| Utility decreased by immunocompromise | Yes | Method dependent | Yes | Yes | Unknown | Yes | No |
| Distinguishes active from latent disease | No | No | No | No | No | Sometimes useful | Yes |
| Stratifies those with LTBI at greatest risk of disease progression | No | No | No | No | No | No | Yes |

In a first aspect of the invention there is provided a method of determining tuberculosis (TB) infection status in an individual comprising:
(i) providing a sample comprising T-cells;
(ii) exposing the sample of (i) to one or more TB antigens;
(iii) identifying T-cells in the sample that are CD4 positive and (a) secrete TNF-α without secreting IFN-γ; or (b) secrete IFN-γ without secreting TNF-α;

By "individual" we refer to any organism capable of being infected with TB. Preferably the individual is a mammal, more preferably selected from cattle, badgers and humans. Most preferably the individual is a human.

By "TB antigens" we refer to any TB protein capable of eliciting an immune response. Examples of TB antigens are tuberculosis purified protein derivative (PPD), ESAT-6, CFP-10, EspC, TB7.7, Rv3879c, Rv3873, Rv3878, PE/PPE proteins, Ag85A/B and TB10.4, Heparin-Binding Haemagglutinin, Rv0440, Rv3875/Rv3874, Rv0140, Rv0384c, Rv2662, Rv3223c, Rv3307, Rv3862c, Rv0079, Rv0081, Rv0574c, Rv1733c, Rv1734c, Rv1998, Rv2006, Rv2007c, Rv2028c, Rv2627c, Rv2629, Rv2630, Rv3132c, Rv0867c, Rv1009, Rv1884c, Rv2389c. Any other TB antigen known in the art could also be used.

In certain embodiments the cells in step (iii) are additionally identified as live T-cells. They may be identified as live cells by any method known in the art, such as the use of either a dead cell marker or a live cell marker. Such markers are well known in the art (e.g. LIVE/DEAD® fixable dead cell stain kits).

Dead cell markers label internal cellular structures via disrupted membranes in dead cells. Other dyes that could be used as dead cell markers are impermeant nucleic acid dyes e.g. EMA, DAPI, SYTOX® Blue/Green/Red, Ethidium homodimer-1, Propidium iodide, 7-MD, monomeric cyanine dyes, Annexin V dyes. Not all of these dyes are suitable for use with formaldehyde fixation unlike the LIVE/DEAD® fixable dead cell stain kits.

The particular subsets of T-cells as specified in steps (iii) and (iv) can be identified by any suitable technique known in the art. However, a preferred technique is that of multi-parameter flow cytometry. This technique is well known in the art as a method which can be used to determine the amount of cells of a certain type in a sample by criteria such as cell phenotype and/or cell function and using a cocktail of visually tagged antibodies specific for multiple markers of cell phenotype or function. The following gating strategy may be used:

Example gating strategy:
1. Gate on live cells i.e. those negative for the dead cell discriminator
2. Gate on singlets using forwards scatter
3. Gate on singlets using side scatter
4. Gate on lymphocytes using light scatter properties.
5. Gate on CD3+ cells
6. Gate on CD4+ cells
7. Define IFN-γ, IL-2 and TNF-α quadrants using fluorescence minus one controls
8. Use Boolean gating to create 7 non overlapping functional subsets including IFN-γ-only secreting and TNF-α-only secreting cells
9. Define CCR7 vs. CD45RA and CCR7 vs. CD127 quadrants using fluorescence minus one controls on functional subsets.
10. Use Boolean gating to select CD45RA$^-$CCR7$^-$CD127$^-$ cells.

In preferred embodiments of the invention, steps (iii) and/or (iv) of the methods of the first aspect of the invention are performed by multi-parameter flow cytometry.

A preferred method of multi-parameter flow cytometry will involve reduction of the number of fluorophore detectors required. It is estimated that the method could be simplified by at least 5 colours to a 6-colour flow cytometry assay. Therefore, the method could be run as a 5-11 colour assay, for example, an 11, 10, 9, 8, 7, 6 or 5 colour flow cytometry assay. This is a realistic target for a diagnostic assay in a clinical setting given the flow cytometry assays currently performed in patients with blood dyscrasias e.g. lymphoma.

In certain embodiments of the invention, the TB infection status determined by the method of the first aspect of the invention corresponds to the presence or absence of TB infection. In other words the method is used to determine if the sample is from an individual that is, or is not, infected with TB.

In certain embodiments the identification of one or more cells in step (iii) determines the presence of TB infection.

In certain embodiments of the invention, the TB infection status determined by the method of the first aspect of the invention corresponds to the presence of an active TB infection (ATB) or a latent TB infection (LTBI). In other words, the method of the invention is able to distinguish between samples from individuals with active TB and those with latent TB.

In certain embodiments the identification of one or more cells in step (iv) determines the presence of an active TB infection.

In certain embodiments the absence of one or more cells in step (iv) determines the presence of a latent TB infection.

In certain embodiments the percentage values calculated in step (v) that determine the presence of an active TB infection are higher than the percentage values calculated in step (v) that determine the presence of a latent TB infection. In other words, the percentage values determined in step (v) for a sample from an individual with active TB will be higher than for a sample from an individual with latent TB.

Preferably, the TB infection status corresponds to an active TB infection when the percentage calculated in step (v) is at least 10% to 40%.

Preferably, the TB infection status corresponds to an active TB infection when the percentage calculated in step (v) is at least 10% to 17.4%.

For example, the TB infection status corresponds to an active TB infection when the percentage calculated in step (v) is at least 10, 11, 12, 13, 14, 15, 15, 17, 18, 19, 20, 21, 22, 23, 24, 25, 26, 27, 28, 29, 30, 31, 32, 33, 34, 35, 36, 37, 38, 39 or 40%.

More preferably, the TB infection status corresponds to an active TB infection when the percentage calculated in step (v) is at least 10, 11, 12, 13, 14, 15, 15, 17, 18, 19, 20, 21, 22, 23, 24, 25, 26, 27, 28, 29 or 30%.

Even more preferably, the TB infection status corresponds to an active TB infection when the percentage calculated in step (v) is at least 17-18%, for example 17.0, 17.1, 17.2, 17.3, 17.4, 17.5, 17.6, 17.7, 17.8, 17.9 or 18.0%.

Most preferably, the TB infection status corresponds to an active TB infection when the percentage calculated in step (v) is at least 17.4%.

Preferably, the TB infection status corresponds to a latent TB infection when the percentage calculated in step (v) is less than or equal to 10% to 40%.

Preferably, the TB infection status corresponds to a latent TB infection when the percentage calculated in step (v) is less than or equal to 17.3% to 40%.

For example, the TB infection status corresponds to latent TB infection when the percentage calculated in step (v) is less than or equal to 10, 11, 12, 13, 14, 15, 15, 17, 18, 19, 20, 21, 22, 23, 24, 25, 26, 27, 28, 29, 30, 31, 32, 33, 34, 35, 36, 37, 38, 39 or 40%.

More preferably, the TB infection status corresponds to an active TB infection when the percentage calculated in step (v) is less than or equal to 10, 11, 12, 13, 14, 15, 15, 17, 18, 19, 20, 21, 22, 23, 24 or 25%.

Even more preferably, the TB infection status corresponds to an active TB infection when the percentage calculated in step (v) is less than or equal to 17-18%, for example 17.0, 17.1, 17.2, 17.3, 17.4, 17.5, 17.6, 17.7, 17.8, 17.9 or 18.0%.

Most preferably, the TB infection status corresponds to a latent TB infection when the percentage calculated in step (v) is less than or equal to 17.3%.

In certain embodiments of the invention, the TB infection status determined by the method of the first aspect of the invention corresponds to the risk of a latent TB infection progressing to an active TB infection. In other words, the method of the invention is able to determine the risk of an individual with a latent TB infection progressing to having active TB.

In one embodiment the risk of a latent TB infection progressing to an active TB infection is determined by the identification of one or more cells in step (iv). In other words, if one or more cells are identified in step (iv), the individual is at risk of progressing from a latent TB infection to active TB.

In one embodiment the risk of a latent TB infection progressing to an active TB infection is proportional (positively correlated) to the percentage value calculated in step (v) of the method. For example, a higher percentage value calculated in step (v) correlates with an increased risk of a latent TB infection progressing to an active TB infection.

In certain embodiments of the invention the TB infection status identified by the method of the first aspect of the invention corresponds to the amount of time elapsed since the individual was originally infected with TB. In other words, the method of the invention is able to determine the relative time since the individual was originally infected with TB.

In one embodiment the time elapsed since the individual was originally infected with TB is inversely proportional (negatively correlated) to the percentage value calculated in step (v). For example, a higher percentage value calculated in step (v) correlates to a shorter amount of time since the individual was originally infected with TB.

A more recently acquired asymptomatic infection is more likely to progress to active TB disease than an infection acquired longer ago. Therefore the proportion or frequency of CD3+CD4+ TNFalpha+ IFNgamma-IL2-CCR7-CD127-CD45RA- may also correlate with the recentness of TB exposure and in some instances may be as high as seen in active TB.

The methods of the invention allow determination of the TB status of an individual regardless of whether or not the individual is also infected with HIV. In other words, the methods of the invention function independently of the HIV status of the individual.

In certain embodiments the individual is infected with HIV. In other embodiments the individual is not infected with HIV, or the HIV infection status of the individual is unknown.

The methods of the invention allow determination of the TB status of an individual regardless of the site of the TB infection. In other words, the methods of the invention function independently of the site of the TB infection.

For example, the individual may be or have been infected with TB in the lung (pulmonary) or at any other site (extrapulmonary), or the site of infection may be unknown.

Examples of extrapulmonary infection sites include the pleura (e.g. in tuberculous pleurisy), the central nervous system (e.g. in tuberculous meningitis), the lymphatic system (e.g. in scrofula of the neck), the genitourinary system (e.g. in urogenital tuberculosis), the bones and joints (e.g. in Pott's disease of the spine), the skin, and gastrointestinal manifestations, among others.

In certain embodiments the individual has been infected with TB at any site. In other words, the site of infection may be pulmonary and/or extrapulmonary. In certain embodiments the site of infection is unknown.

In certain embodiments of the invention the sample provided in step (i) of the methods of the first aspect of the invention is a blood sample, preferably a peripheral blood mononuclear cell (PBMC) sample. Alternatively, a bronochoalveolar lavage (BAL) or cerebral spinal fluid (CSF) sample may be used.

In certain embodiments of the invention, the method is 70-100% sensitive and/or 80-100% specific. In one embodiment the method is 100% sensitive and/or 93% specific. Sensitivity and specificity are calculated using receiver operator curve analysis. This calculates a range of sensitivity and specificities depending on which percentage cut-off is drawn e.g. for a cut-off of >19.05% MTB-specific TNF-α only secreting cells that are CD45RA-CCR7-CD127- sensitivity is 83.3% and specificity is 100%.

In certain embodiments of the invention an additional step in the method of the first aspect of the invention is first performed in order to determine that the sample of cells is either infected with MTB or is obtained from a subject infected with MTB.

For example, this additional first step may be performed using an ELISpot (Enzyme-Linked Immunosorbent Spot) platform. IGRA (interferon-gamma release assays), Immune based assays, tuberculin skin tests and/or Quantiferon can also be used.

In a second aspect of the invention there is provided a composition comprising a plurality of antibodies or antigen-binding fragments thereof that binds to each of CD4, CCR7 and CD127 and wherein the plurality comprises antibodies or antigen-binding fragments thereof that are individually specific for each of CD4, CCR7 and CD127.

In other words, the composition as a whole is able to bind to each of CD4, CCR7 and CD127 and comprises antibodies or antigen-binding fragments thereof that are individually able to bind only one of CD4, CCR7 and CD127.

In one embodiment the plurality of antibodies or antigen-binding fragments thereof additionally binds to each of TNF-α and IFN-γ and additionally comprises antibodies or antigen-binding fragments thereof that are individually specific for each of TNF-α, and IFN-γ.

In other words, the composition as a whole is able to bind to each of CD4, CCR7, CD127, TNF-α, and IFN-γ and comprises antibodies or antigen-binding fragments thereof that are individually able to bind only one of CD4, CCR7, CD127, TNF-α, and IFN-γ.

In a third aspect of the invention there is provided a composition comprising a plurality of antibodies or antigen-binding fragments thereof that binds to each of CD4, TNF-α, and IFN-γ and wherein the plurality comprises antibodies or antigen-binding fragments thereof that are individually specific for each of CD4, TNF-α, and IFN-γ.

In a fourth aspect of the invention there is provided a composition comprising a plurality of antibodies or antigen-binding fragments thereof that binds to each of CCR7 and CD127 and wherein the plurality comprises antibodies or antigen-binding fragments thereof that are individually specific for each of CCR7 and CD127.

In certain embodiments, the plurality of antibodies or antigen-binding fragments of the compositions of the second, third or fourth aspects is additionally able to bind to one or more of CD3, CD8, CD45RA, IL-2 and/or dead cells and the plurality additionally comprises antibodies or antigen-binding fragments thereof that are individually specific for the one or more of CD3, CD8, CD45RA, IL-2 and/or dead cells.

In a preferred embodiment, the plurality of antibodies or antigen-binding fragments of the compositions of the second, third or fourth aspects is additionally able to bind to CD45RA and the plurality additionally comprises antibodies or antigen-binding fragments thereof that are individually specific for CD45RA.

In a preferred embodiment, the plurality of antibodies or antigen-binding fragments of the compositions of the second, third or fourth aspects is additionally able to bind to IL-2 and the plurality additionally comprises antibodies or antigen-binding fragments thereof that are individually specific for IL-2.

In a preferred embodiment, the plurality of antibodies or antigen-binding fragments of the compositions of the second, third or fourth aspects is as a whole additionally able to bind to CD3 and the plurality additionally comprises antibodies or antigen-binding fragments thereof that are individually specific for CD3.

The antigen-binding fragment may be selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

Also included within the scope of the invention are modified versions of antibodies and an antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

In certain embodiments the plurality of antibodies or antigen-binding fragments thereof is fixed to a solid support.

In certain embodiments the antibodies or antigen-binding fragments thereof with a particular specificity are separately detectable to those with a different specificity.

In other words an antibody or antigen-binding fragment thereof which is specific for a particular target can be detected as a separate entity to an antibody or antigen-binding fragment thereof which is specific for a different target. In this context 'target' refers to any of CD3, CD4, CD8, CD45RA, CCR7, CD127, TNF-α, IFN-γ or IL-2.

In a preferred embodiment the antibodies or antigen-binding fragments thereof are visually detectable.

The antibodies or antigen-binding fragments thereof may be labelled in order to allow their detection. For example, they may be labelled with a fluorescent label (e.g. a fluorophore) or with a radio label.

Multiple examples of suitable labels such as fluorophores are well known in the art.

Fluorophores of interest include, but are not limited to fluorescein dyes (e.g. fluorescein dT, 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE)), cyanine dyes such as Cy5, dansyl derivatives, rhodamine dyes (e.g. tetramethyl-6-carboxyrhodamine (TAMRA), ATTO dyes (such as ATTO 647N) and tetrapropano-6-carboxyrhodamine (ROX)), DABSYL, DABCYL, cyanine, such as Cy3, anthraquinone, nitrothiazole, and nitroimidazole compounds, or other non-intercalating dyes.

Preferred possible fluorophores include, amongst others, BD Horizon™ violet laser dyes e.g. BD Horizon™ V450, Alexa Fluor® dyes e.g. Alexa Fluor® 488, Fluorescein isothiocyanate (FITC), R-phycoerythrin (PE), PECy™ 5, PerCP, PerCPCy™ 5.5, PE-Cy™7, Allophycocyanin (APC), APC-Cy™ 7, APC-H7, Qdot dyes e.g. Qdot 605.

Particularly preferred fluorophores include, but are not limited to PE-CF594, AF700, QDot605, Qdot655, PE-Cy7, PerCP-Cy5.5, APC-Cy7, BV570, V450, PE, FITC, APC, Biotin, PE-Cy5.

Exemplary fluorophores are used as in the following antibodies used in the methods described herein: LIVE/DEAD® Fixable Dead Cell Stain Kits, aqua, (Invitrogen), CD3-APC-Alexa Fluor®750, CD4-Qdot®605, CD45RA-Qdot®655 (Invitrogen), CD8-APC, CCR7-PE-Cy™ 7, CD127-FITC (BD Biosciences), PD-1-PerCP/Cy5.5 (Biolegend). IFN-γ-V450, IL-2-PE and TNF-α-AlexaFluor 700 (BD Biosciences)

As used herein, "fluorophore" (also referred to as fluorochrome) refers to a molecule that, when excited with light having a selected wavelength, emits light of a different wavelength.

In a third aspect of the invention the composition of the second aspect is for use in diagnosing an active or latent TB infection.

In a fourth aspect of the invention the composition of the second aspect is for use in treating a TB infection wherein the use comprises identifying if an individual has an active or latent TB infection and subsequently administrating the most appropriate treatment for that infection. For example, if the individual is shown to have active TB, then treatment appropriate for treating active TB will be administered.

In a fifth aspect of the invention there is provided a method of treating a subject infected with TB comprising:
(a) conducting the method of any previous claim; and
(b) administrating the most appropriate treatment to the subject depending on the outcome of the step (a)

For example, if the individual is shown by step (a) to have an active TB infection, then a treatment appropriate for treating active TB will be administered in step (b). As an alternative example, if the individual is shown by step (a) to have a high risk of progressing from a latent TB infection to active TB, then an appropriate treatment will be administered in step (b) (e.g. a treatment for treating active TB will be administered in step (b)).

As a further example, an individual co-infected with HIV could be recommended to start highly active antiretroviral therapy (HAART) if shown to have LTBI.

In a sixth aspect of the invention there is provided a kit for determining tuberculosis (TB) infection status in an individual comprising:
(i) a composition comprising a plurality of antibodies or antigen-binding fragments thereof that binds to each of CD4, CCR7 and CD127 and wherein the plurality comprises antibodies or antigen-binding fragments thereof that are individually specific for each of CD4, CCR7 and CD127;
(ii) a composition comprising a plurality of antibodies or antigen-binding fragments thereof that binds to each of TNF-α and IFN-γ and wherein the plurality comprises antibodies or antigen-binding fragments thereof that are individually specific for each of TNF-α, and IFN-γ; and
(iii) instructions for use.

In other words, the composition (i) of the kit is a composition which as a whole is able to bind to each of CD4, CCR7 and CD127 and comprises antibodies or antigen-binding fragments thereof that are individually able to bind only one of CD4, CCR7 and CD127; and the composition (ii) of the kit is a composition which as a whole is able to bind to each of TNF-α, and IFN-γ and comprises antibodies or antigen-binding fragments thereof that are individually able to bind only one of TNF-α, and IFN-γ.

In a seventh aspect of the invention there is provided a kit for determining tuberculosis (TB) infection status in an individual comprising:
(i) a composition comprising a plurality of antibodies or antigen-binding fragments thereof that binds to each of CD4, TNF-α and IL-2 and wherein the plurality comprises antibodies or antigen-binding fragments thereof that are individually specific for each of CD4, TNF-α and IL-2;
(ii) a composition comprising a plurality of antibodies or antigen-binding fragments thereof that binds to each of CCR7 and CD127 and wherein the plurality comprises antibodies or antigen-binding fragments thereof that are individually specific for each of CCR7 and CD127; and
(iii) instructions for use.

In other words, the composition (i) of the kit is a composition which as a whole is able to bind to each of CD4, TNF-α and IL-2 and comprises antibodies or antigen-binding fragments thereof that are individually able to bind only one of CD4, TNF-α and IL-2; and the composition (ii) of the kit is a composition which as a whole is able to bind to each of CCR7 and CD127 and comprises antibodies or antigen-binding fragments thereof that are individually able to bind only one of CCR7 and CD127.

In an eighth aspect of the invention there is provided a kit for determining tuberculosis (TB) infection status in an individual comprising:
(i) a composition comprising a plurality of antibodies or antigen-binding fragments thereof that binds to each of CD4, CCR7, CD127, TNF-α and IFN-γ and wherein the plurality comprises antibodies or antigen-binding fragments thereof that are individually specific for each of CD4, CCR7, CD127, TNF-α and IFN-γ; and
(ii) instructions for use.

In other words, the composition (i) of the kit is a composition which as a whole is able to bind to each of CD4, CCR7, CD127, TNF-α, and IFN-γ and comprises antibodies or antigen-binding fragments thereof that are individually able to bind only one of CD4, CCR7, CD127, TNF-α, and IFN-γ.

In certain embodiments of the kit of the sixth, seventh and eight aspects, the plurality of antibodies or antigen-binding fragments of the composition of (i) and/or (ii) is additionally able to bind to one or more of CD3, CD8, CD45RA, IL-2 and/or dead cells and additionally comprises antibodies or antigen-binding fragments thereof that are individually specific for the one or more of CD3, CD8, CD45RA, IL-2 and/or dead cells.

In certain embodiments of the kit of the sixth, seventh and eight aspects, the plurality of antibodies or antigen-binding fragments of the composition of (i) and/or (ii) is additionally able to bind to CD45RA and additionally comprises antibodies or antigen-binding fragments thereof that are individually specific for CD45RA.

In certain embodiments of the kit of the sixth, seventh and eight aspects, the plurality of antibodies or antigen-binding fragments of the composition of (i) and/or (ii) is additionally able to bind to CD3 and additionally comprises antibodies or antigen-binding fragments thereof that are individually specific for CD3.

In certain embodiments of the kit of the sixth, seventh and eight aspects, the plurality of antibodies or antigen-binding fragments of the composition of (i) and/or (ii) is additionally able to bind to IL-2 and additionally comprises antibodies or antigen-binding fragments thereof that are individually specific for IL-2.

In certain embodiments the kit of the sixth and seventh aspects additionally comprises one or more TB antigens, a live and/or dead cell discriminator, and/or a positive control.

Example TB antigens are described above. Example dead cell discriminators (e.g. dead cell markers) are described above.

Example positive controls include PMA-Ionomycin for stimulating the sample, PMA plus calcium ionophore, lipopolysaccharide (LPS), staphylococcal enterotoxin B (SEB), Anti CD3 plus Anti CD28, phytohemagglutinin (PHA). Activated human cell sets that have been screened for cytokine production may also be used.

One particular exemplary kit may include one or more of the following components:
a) Positive control, test antigen
b) Dead cell discriminator
c) Cocktail of cell surface fluorophore-conjugated antibodies
d) Fixing and permeabilising buffer
e) Cocktail of intracellular fluorophore-conjugated antibodies
f) Wash buffer(s)
g) Test plate
(optional h) compensation beads In an eighth aspect of the invention there is provided the use of a kit of the sixth or seventh aspect in a method of the first aspect.

Definitions and Abbreviations

By "CD3", "CD4" and "CD8" we refer to cluster of differentiation 3, 4 and 8, respectively.
By "CCR7" we refer to C-C chemokine receptor 7
By "CD127" we refer to cluster of differentiation 127, also known as interleukin-7 receptor alpha.

By "CD45RA" we refer to cluster of differentiation 45 RA isoform.

By "IFN-γ" we refer to interferon-gamma.

By "IL-2" we refer to interleukin-2.

By "TNF-α" we refer to tumour necrosis factor-alpha.

By "+" we mean positive. In other words the particular immunological molecule/marker the + is associated with is present.

By "−" we mean negative. In other words the particular immunological molecule/marker the − is associated with is absent.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to a particular antigen.

The term "individual" encompasses all organisms. Examples of those organisms include mammals such as humans, cows, badgers, dogs, cats, goats, sheep, and pigs. Preferably the individual is human.

Examples embodying an aspect of the invention will now be described with reference to the following figures in which:

Graphs show frequency and median of CD4+(B) and CD8+(C) cells secreting IFN-γ and TNF-α in response to overnight stimulation with PPD or RD1-peptides in participants with ATB versus LTBI. Those with HIV co-infection (filled circles) and without HIV co-infection (open circles) are indicated. Results were analysed by Mann Whitney U test; and p values of <0.05 were considered significant.

Figure 2:
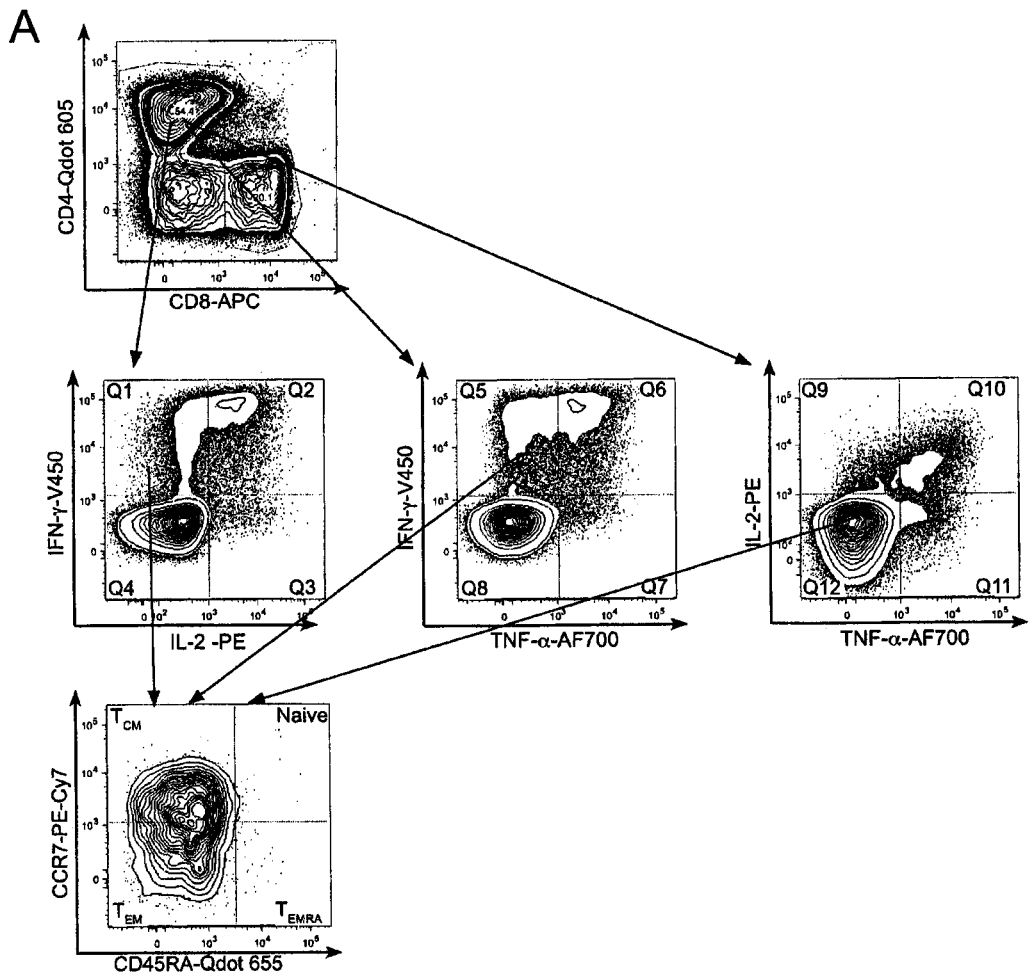

FIG. 2 shows the cell surface phenotype of CD4+ cell functional subsets is influenced by TB disease stage CD4+ cell functional subsets were examined for CD45RA and CCR7 expression in active versus LTBI in those with a positive response.

(A) An example gating strategy for a PPD-specific CD4+ IFN-γ-only secreting subset is demonstrated using representative plots from an individual with ATB. Each CD3+CD4+ (top row) functional subset e.g. IFN-γ-only-secreting cells (middle row) was analysed for expression of CD45RA and CCR7 (bottom row).

(B) Graphs show the percentage (and median percentage) of PPD-stimulated CD4+ IFN-γ-only (page 7/22), TNF-α-only (page 8/22) and IL-2-only (page 9/22) cells that were CD45RA-CCR7+(TCM) (top chart) and CD45RA-CCR7− (TEM) (bottom chart) in patients with ATB and LTBI. The first two pages are representative of changes observed in active versus LTBI in all MTB-specific (responding to PPD and RD-1-peptides) CD4+ functional subsets except IL-2-only-secreting cells. Those with HIV co-infection (filled circles) and without HIV co-infection (open circles) are indicated. Results were analysed by Mann Whitney U test; and p values of <0.05 were considered significant.

Figure 3:
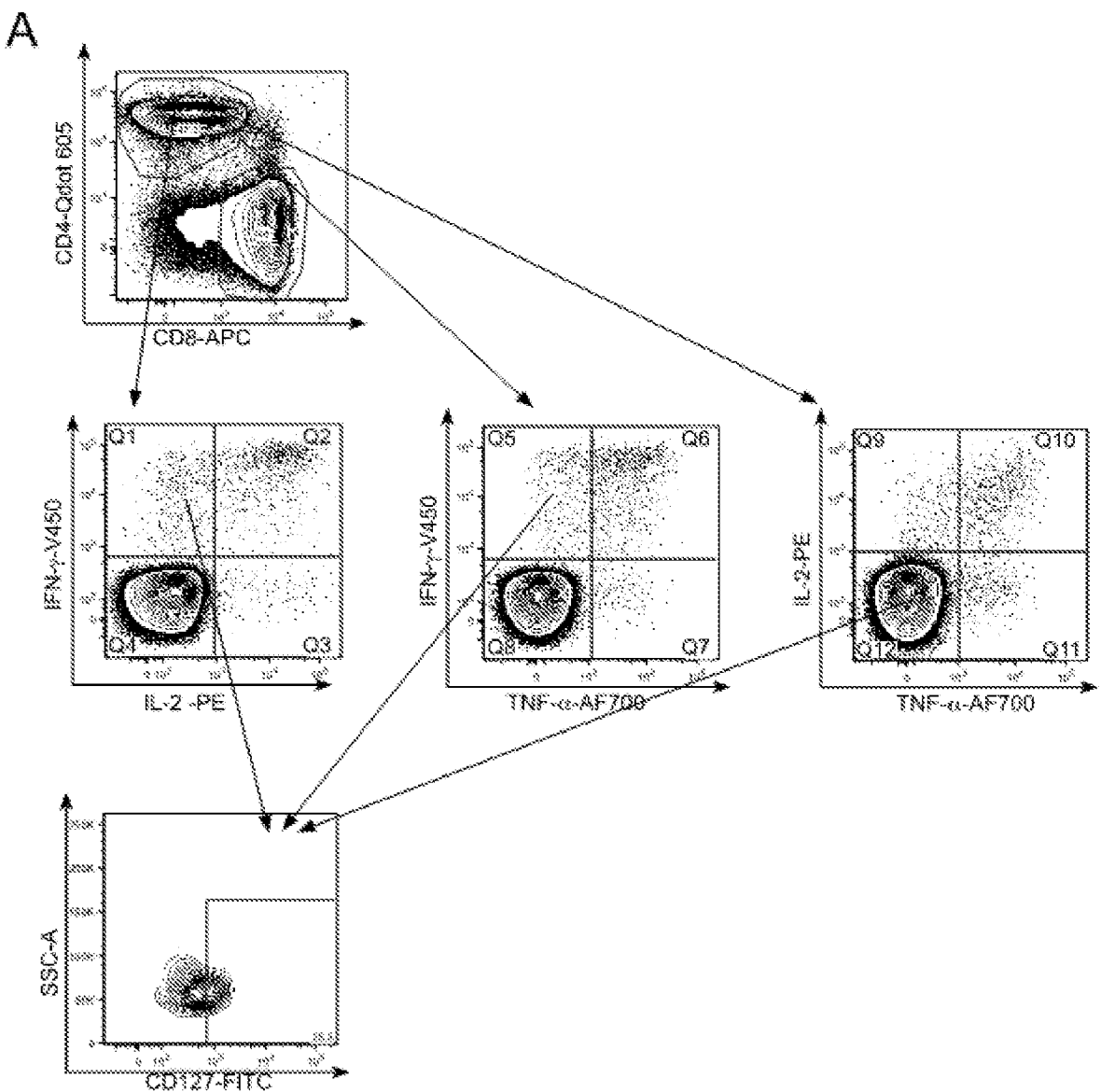

FIG. 3 shows the percentage of MTB-specific CD4+ functional T-cell subsets expressing CD127 is influenced by stage of TB infection and CD4 count CD3+CD4+ functional cell subsets were examined for CD127 expression.

(A) A representative gating strategy is shown. PBMCs from an individual with LTBI infection were stimulated overnight with PPD, and CD3+CD4+ cells (top row) were gated for cytokine secretion e.g. IFN-γ-only-secreting subset (middle row) and analysed for expression of CD127 (bottom row).

(B) Graphs show percentage (and median percentage) of cells expressing CD127 from positive responders in CD4+ IFN-γ-only—(top row), TNF-α-only—(middle row) and IFN-γ- and TNF-α-dual-secreting (bottom row) cell subsets following stimulation with PPD (page 11/22) and RD1-peptides (page 12/22) in ATB and LTBI. Patients with HIV co-infection (filled circles) and without HIV co-infection (open circles) are indicated. Results were analysed by Mann Whitney U test; and p values of <0.05 were considered significant.

(C) Graphs show correlations of CD4 cells/pi with the percentage of CD4+ PPD-specific cells secreting all three cytokines (top left), IFN-γ-only (top right), TNF-α and IL-2 (bottom left) and TNF-α-only (bottom right) that expressed CD127 in patients with HIV co-infection. Patients with TB (filled circles) and LTBI (open circles) are indicated. Spearman's rank correlation coefficient, corresponding p values and lines of best fit are shown.

Figure 4:
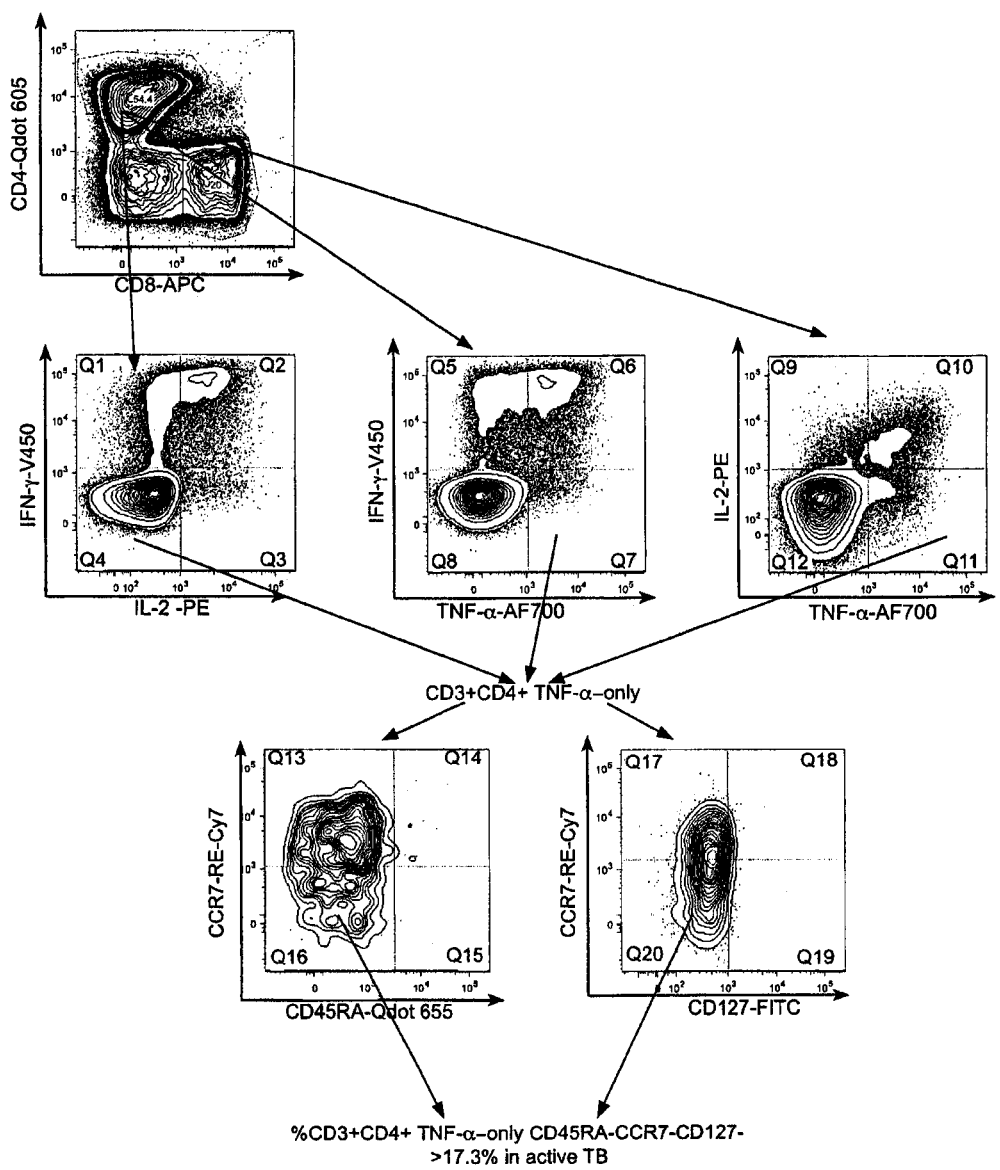

FIG. 4 shows combining functional subset analysis with memory phenotype reveals a potentially powerful biomarker to distinguish active and LTBI Boolean gating was used to analyse the percentage of PPD-specific CD4+ TNF-α-only-secreting cells that had the phenotype TEFF (CD45RA−CCR7−CD127−) in active and LTBI.

A representative gating strategy is shown for individuals with ATB (A) and LTBI (B). (C) Graphs at the top of each page show the percentage (and median percentage) of PPD or RD-1 peptide-specific CD4+ TNFα-only and IFNγ-only cells from responders that were TEFF. Cut off values for distinguishing ATB from LTBI are shown as dotted lines, and corresponding ROC curves are shown in bottom chart on each page. A cut off of 17.3% of TNF-α-only cells of TEFF phenotype distinguished ATB from LTBI with 100% sensitivity (95% CI 73.5-100.0) and 92.9% specificity (95% CI 66.1-99.8) (table 2). In ROC analysis, area under the curve was 0.99 (95% CI 0.97-1.01; p<0.0001) (FIG. 4C). A cut off of 34.5% for PPD-specific IFN-γ-only cells gave a sensitivity of 100% (95% CI 73.5 to 100.0) and specificity of 84.2% (95% CI 60.42-96.6); a cut off of 33.8% for RD-1-specific TNF-α-only cells gave a sensitivity of 100% (95% CI 54.07 to 100.0) and specificity of 75.0% (95% CI 34.91 to 96.8); and a cut off of 49.3% of RD-1-specific IFN-γ-only cells gave a sensitivity of 100% (95% CI 66.4-100.0) and specificity of 75.0% (95% CI 42.8-94.5).

(D) Graphs show the percentage (and median percentage) of PPD-specific CD4+ TNFα-only and IFNγ-only cells that were TEFF in patients with extrapulmonary TB (EPTB) and pulmonary TB (PTB). Patients with HIV co-infection (filled circles) and without HIV co-infection (open circles) are indicated. Results were analysed by Mann Whitney U test; and p values of <0.05 were considered significant.

Figure 5:
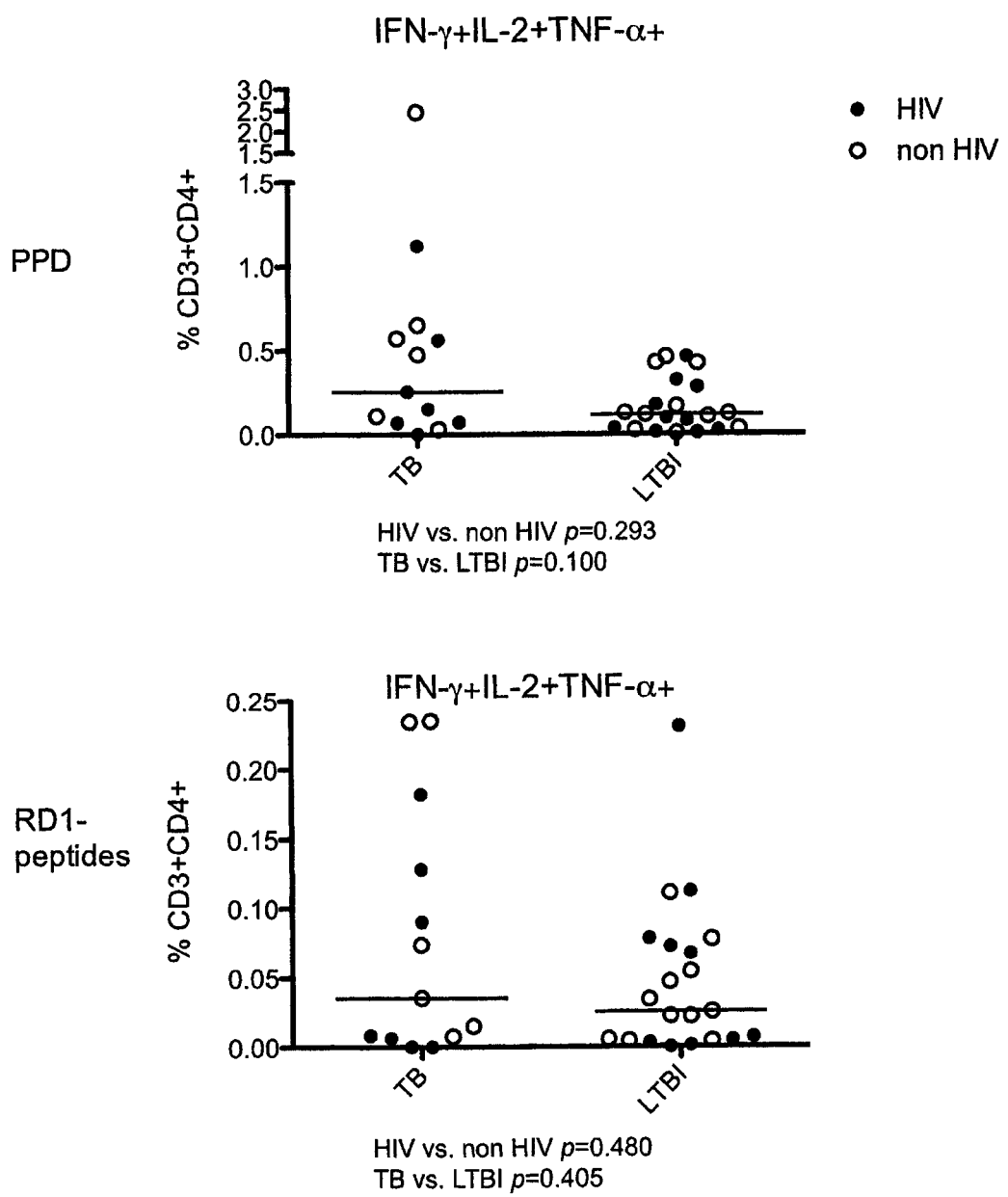

FIG. 5 shows there was no difference in the frequency of tri-functional cells between those with ATB or LTBI or HIV-infected versus uninfected responding to PPD (top row) or RD-1 peptides (bottom row)

Patients with HIV co-infection (filled circles) and without HIV co-infection (open circles) are indicated. Results were analysed by Mann Whitney U test; and p values of <0.05 were considered significant.

Figure 6:
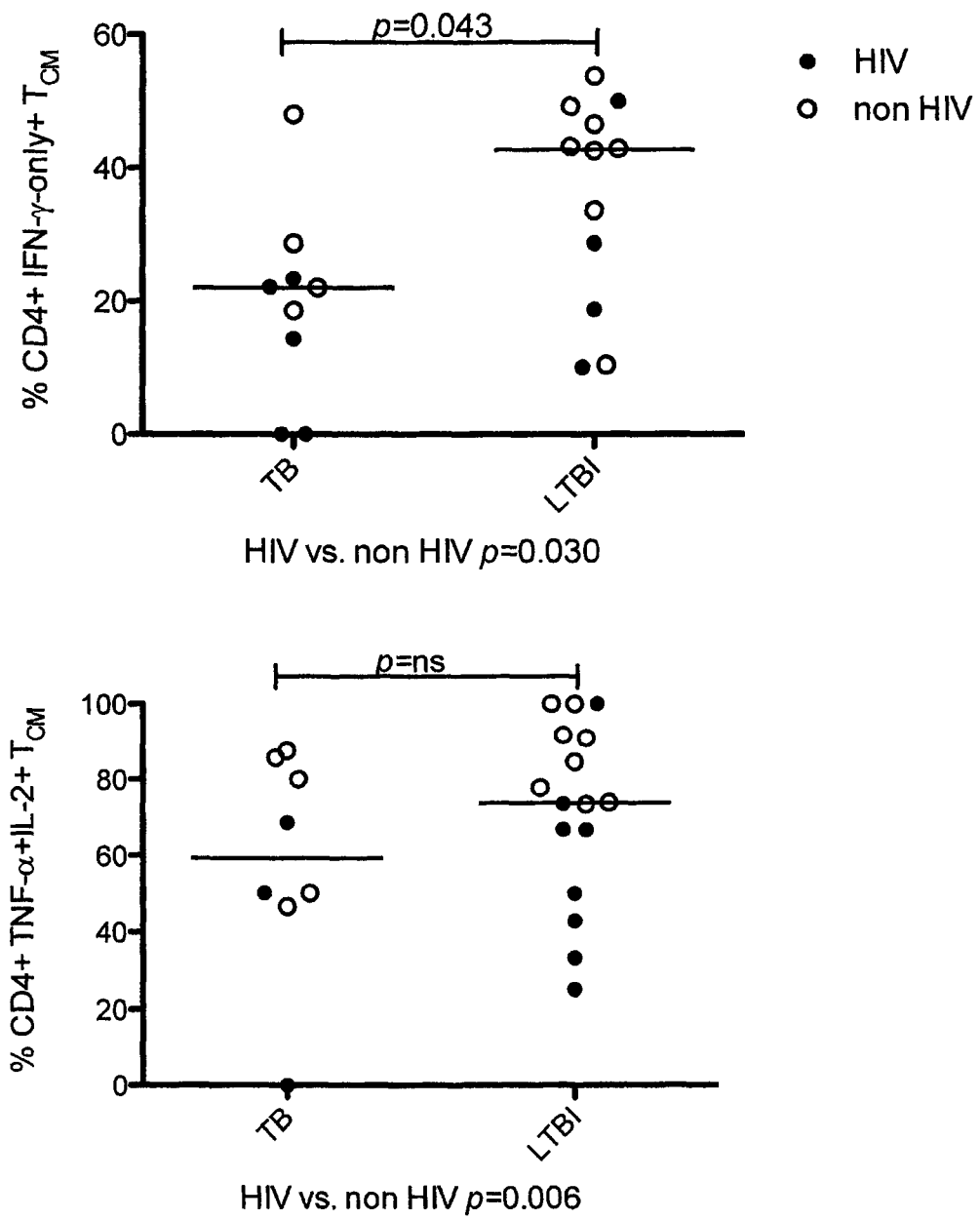

FIG. 6 shows there was no difference in the proportion of any CD4+ functional subsets that were TCM except for RD-1-peptides-specific cells secreting IFN-γ only (top row) and TNF-α and IL-2 (bottom row)

Patients with HIV co-infection (filled circles) and without HIV co-infection (open circles) are indicated. Results were analysed by Mann Whitney U test; and p values of <0.05 were considered significant.

Figure 7:
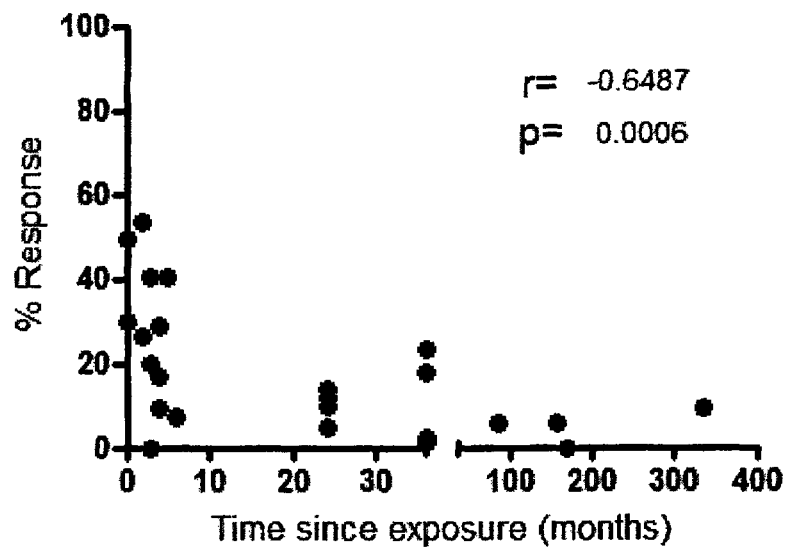
Figure 7:
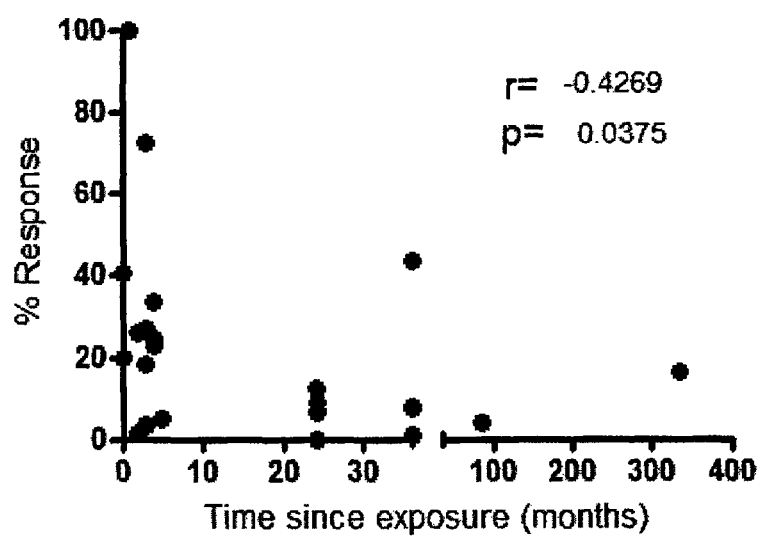

FIG. 7 shows the inverse correlation of the proportion of PPD-specific or ECR-specific TNF-α-only T cells that are CD45RA–CCR7–CD127– with time since exposure to TB Proportion of (a) PPD-specific and (b) ECR-specific TNF-α-only T cells that are CD45RA–CCR7–CD127– against estimated time since TB exposure. Results were analysed by Spearman's Rank Correlation Coefficient.

EXAMPLES

Methods Used in the Examples

Participants were prospectively enrolled from three clinical centres in London, UK during the period January 2008-February 2011 under National Research Ethics Service approval (07/H0712/85). Participants were ≥18 years, provided written, informed consent and were eligible if under clinical investigation for ATB (active TB), undergoing LTBI (latent tuberculosis infection) screening or had recognised TB risk factors e.g. known TB contact.

Suspected ATB was confirmed microbiologically by the clinical diagnostic laboratory. LTBI was defined as a positive response to RD-1 antigens in either T-SPOT.TB (carried out in routine clinical work up) or MTB IFN-γ ELISpot (carried out for the current study) in the absence of symptomatic, microbiological or radiological evidence of ATB.

Presence of HIV infection was confirmed by 3rd or 4th generation sero-assay performed by the clinical diagnostic laboratory and using HIV-1 type specific EIA, according to national standards. HIV viral load (VL) and CD4 T-lymphocyte counts were assayed in the local Clinical Pathology Association-accredited diagnostic laboratories at the time of study recruitment. HIV diagnostics were available for all patients with ATB (in line with the national screening policy) and the majority of those with LTBI; the remainder had no risk factors for HIV and normal CD4:CD8 lymphocyte ratios, and were classified as HIV-uninfected.

The demographic characteristics of the study population are shown in Table 1.

TABLE 1

| Demographics and clinical test results of participants | | | | | | | | | | |
|---|---|---|---|---|---|---|---|---|---|---|
| | HIV & TB | | TB | | HIV & LTBI | | LTBI | | Total | |
| | 7 | (%) | 6 | (%) | 10 | (%) | 11 | (%) | 34 | (%) |
| Median (IQR) age | 43 | (40.5-52.4) | 34.5 | (28.0-56.0) | 36 | (24.0-39.0) | 33 | (31.0-35.5) | 35.5 | (31.3-40.8) |
| Sex | | | | | | | | | | |
| Male | 4 | (57.1) | 3 | (50.0) | 6 | (60.0) | 4 | (36.4) | 17 | (50.0) |
| Female | 3 | (42.9) | 3 | (50.0) | 4 | (40.0) | 7 | (63.6) | 17 | (50.0) |
| Ethnicity | | | | | | | | | | |
| Black African | 5 | (71.4) | 1 | (16.7) | 8 | (80.0) | 6 | (54.5) | 20 | (58.8) |
| Asian | 1 | (14.3) | 3 | (50.0) | 0 | (0.0) | 3 | (27.3) | 7 | (20.6) |
| Caucasian | 1 | (14.3) | 2 | (33.3) | 2 | (20.0) | 2 | (18.2) | 7 | (20.6) |
| BCG vaccination | | | | | | | | | | |
| Yes | 5 | (71.4) | 3 | (50.0) | 9 | (90.0) | 8 | (72.7) | 25 | (73.5) |
| No | 1 | (14.3) | 2 | (33.3) | 0 | (0.0) | 2 | (18.2) | 5 | (14.7) |
| unknown | 1 | (14.3) | 1 | (16.7) | 1 | (10.0) | 1 | (9.1) | 4 | (11.8) |
| Microbiological (smear/culture) confirmation | | | | | | | | | | |
| Positive | 7[a] | (100.0) | 6[b] | (100.0) | NA | NA | NA | NA | 13 | (100.0) |
| negative | 0 | (0.0) | 0 | (0.0) | NA | NA | NA | NA | 0 | (0.0) |
| HIV test | | | | | | | | | | |
| Positive | 7 | (100.0) | 0 | (0.0) | 10 | (100.0) | 0 | (0.0) | 17 | (50.0) |
| negative | 0 | (0.0) | 6 | (100.0) | 0 | (0.0) | 6 | (54.5) | 12 | (35.3) |
| not done | 0 | (0.0) | 0 | (0.0) | 0 | (0.0) | 5[b] | (45.5) | 5 | (14.7) |

All subjects tested positive in one or more of the tuberculin skin test, TSPOT.TB, QuantiFERON ®-TB Gold In-Tube or MTB IFN-γ ELISpot, performed clinically or for the current study.
IQR = interquartile range

[a]Ten patients with TB had not started treatment at the point of recruitment, two had received <14 days treatment, and one had received ≥14 days treatment
[b]All participants without clinical need for HIV testing had normal CD4:CD8 ratios IFN-γ MTB ELISpot Fresh or frozen peripheral blood mononuclear cells (PBMCs), $2.5 \times 10^5$ per well, were stimulated overnight (37° C., 5% $CO_2$, 16-20 h) in an IFN-γ ELISpot plate (Mabtech) with phytohemagglutinin (PHA; positive control; Sigma-Aldrich), Tuberculin Purified Protein Derivative (PPD; Statens Serum Institute) or pools of MTB-specific 15-mer overlapping peptides covering each of ESAT-6, CFP-10, EspC, TB7.7, Rv3879c, Rv3873 and Rv3878. Unstimulated cells were used as a negative control. The IFN-γ ELISpot assay was performed as previously described (Dosanjh D P et al. Ann Intern Med 2008; 148:325-36).

Intracellular cytokine staining and polychromatic flow cytometry: Thawed PBMCs ($3-5 \times 10^6$ per well) were cultured for 16 h (37° C., 5% $CO_2$) in 10% human serum (Sigma-Aldrich) in RPMI-1640 (Sigma-Aldrich) at a concentration of $1 \times 10^1$ cells/ml. Cells were stimulated with PMA-Ionomycin (positive control); (Sigma-Aldrich; 500 ng/ml final concentration), PPD (16.7 μg/ml final concentration) or a cocktail of peptides spanning the length of three highly immunodominant MTB-specific RD1-associated antigens, ESAT-6, CFP-10 and EspC (10 μg/ml final concentration per peptide) (Millington K A et al. Proc Natl Acad Sci USA 2011; 108:5730-5). Unstimulated cells were used as a negative control.

After two hours, monensin (2 μM final concentration) was added. Following stimulation, cells were washed and stained with a dead cell marker (LIVE/DEAD™ Fixable Dead Cell Stain Kits, aqua, Invitrogen) for 30 minutes at 4° C. in phosphate buffered saline (PBS). Cells were then washed in PBS and placed in FC block buffer (10% human serum in filtered FACS solution (0.5% bovine serum albumin and 2 mM EDTA in PBS)) for 20 minutes at 4° C. before staining with a pre-titrated and optimised antibody cocktail with fluorochrome-conjugated antibodies against CD3-APC-Alexa Fluor® 750, CD4-Qdot®605, CD45RA-Qdot®655 (Invitrogen), CD8-APC, CCR7-PE-Cy™ 7, CD127-FITC (BD Biosciences) and PD-1-PerCP/Cy5.5 (Biolegend). After washing, the cells were fixed and permeabilised using BD Cytofix/Cytoperm™ Fixation/Permeabilization kit (BD Biosciences) for 20 minutes at 4° C. The cells were washed twice with Perm/Wash solution (BD Biosciences) then stained with pre-titrated fluorochrome-conjugated antibodies in Perm/Wash solution with IFN-γ-V450, IL-2-PE and TNF-α-AlexaFluor 700 (BD Biosciences) for 30 minutes at 4° C. $1 \times 10^6$ events (where possible) were acquired straightaway using a BD LSR-II flow cytometer. Anti-Rat and Anti-Mouse Ig compensation beads (BD Biosciences) were used to set compensation parameters. Fluorescence minus one (FMO) controls were used in each experiment to set gates.

Data Analysis and Thresholds

The data was analysed on FlowJo version 9.4.4 © TreeStar, Inc. Events were gated on live cells, singlets and lymphocytes using forward and side scatter properties. CD3+CD4+ and CD3+CD8+ subsets were defined. Gating controls were used to define IFN-γ, IL-2 and TNF-α responses and surface marker expression.

For phenotypic analysis of MTB-specific cells, only participants with a positive response were included. Positive responders were defined as those with a response that was ≥2 times the background (in unstimulated but fully stained samples) and >0.001% of CD3+CD4+ or CD3+CD8+ cells. This cut-off was used because we did not use co-stimulation to enhance responses, and we normalised to background (unstimulated) data before applying the cut-off (rather than classifying background as negligible). A strict cut-off meant only antigen-specific cells were included in the phenotypic analysis.

Statistical Analysis

Statistical analysis was conducted using IBM SPSS Statistics version 20 and GraphPad Prism version 5.00 for Mac OS X, GraphPad Software, California USA. TB disease stage compared all TB (n=13) vs. all LTBI (n=21) regardless of HIV status, the impact of HIV compared all HIV-infected (n=17) vs. uninfected (n=17) regardless of TB disease stage and across all four subgroups. The 2-tailed Mann-Whitney U test was used for non-parametric two-sample comparisons. Spearman's rank correlation coefficients were used to test correlations. Receiver operator characteristic (ROC) curve defined the sensitivity and specificity of the diagnostic approach.

Figure 1:
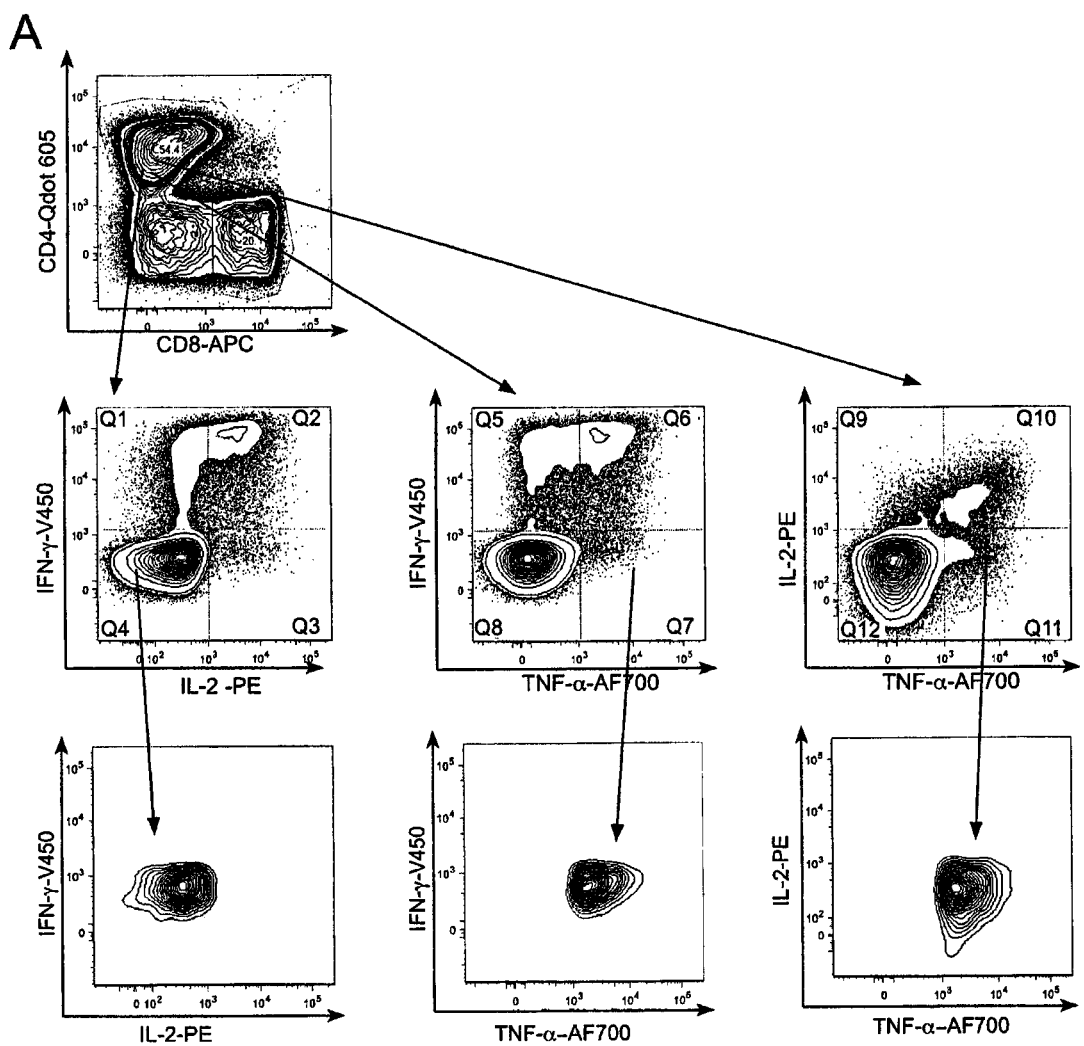
FIG. 1 shows the frequency of IFN-γ and TNF-α secreting CD4+ and CD8+ cell subsets are increased in ATB (A) Example gating strategy for the CD4+ TNF-α-only-secreting subset using representative plots from an individual with ATB whose cells were stimulated overnight with PPD is shown. Cells were gated on live singlets (not shown) and CD3+CD4+ cells (top row), then according to IFN-γ, IL-2 and TNF-α expression using FMOs (middle row). Boolean gating was used to define individual non-overlapping functional subsets, for example the TNF-α-only subset which did not express IFN-γ or IL-2 (bottom row).

Example 1—the Frequency of CD4+ and CD8+ Cells with an IFN-γ+ and TNF-α+ Response was Increased in ATB We first examined the frequency of CD4+ and CD8+ functional effector cell subsets. Boolean gating was used to create individual non-overlapping subsets by combining data in 3 dimensions (FIG. 1A). The frequency of PPD-specific CD4+ IFN-γ-only, TNF-α-only and IFN-γ/TNF-α-dual-secreting cells was higher in ATB compared with LTBI (p=0.003, 0.002 and 0.002, respectively) (FIG. 1B). A similar relationship was seen for RD1-peptide-specific CD4+ IFN-γ-only-secreting cells (not significant; data not shown), and IFN-γ/TNF-α-dual-secreting cells (p=0.017) (FIG. 1B).

The presence of HIV-infection was not associated with an altered frequency of these cell subsets. We observed no difference in the frequency of tri-functional cells in patients with ATB compared with those with LTBI (FIG. 5).

The majority of participants with ATB, but not LTBI, had a CD8+ IFN-γ response (PPD: 12/13 for ATB vs 6/21 for LTBI, RD1-peptides: 10/13 for ATB vs 11/21 for LTBI). The frequencies of PPD- and RD1-peptide-specific CD8+ IFN-γ-only-producing cells were significantly higher in ATB than in LTBI (p=0.017 and 0.016, respectively), as was the frequency of CD8+ PPD-specific cells secreting both IFN-γ and TNF-α (p=0.013) (FIG. 1C).

HIV co-infection was (non-significantly) associated with a reduced frequency of PPD-specific IFN-γ/TNF-α-dual and TNF-α-only responses in ATB compared with HIV-negativity (p=0.051 for both). In the HIV-uninfected TB group the percentages of these PPD-specific CD8+ cells were significantly higher than in LTBI (p=0.008 and 0.022 respectively). Similarly the frequency of cells secreting IFN-γ-only were significantly higher in ATB compared with LTBI in HIV-uninfected (p=0.023). These CD8+ effector functional subsets were therefore related to mycobacterial load analogously to equivalent CD4+ subsets but the impact of HIV co-infection was more profound.

Example 2—PPD-Specific and RD1-Peptide-Specific CD4+ Cellular Differentiation was Increased in ATB Versus LTBI We analysed the memory phenotype of the CD4+ functional subsets as putative correlates of mycobacterial pathogen load. Non-responders were excluded. Each T-cell functional subset was gated for expression of CD45RA and CCR7 (FIG. 2A). Memory phenotypes of functional subsets were defined as naïve CD45RA+CCR7+, central memory (TCM) CD45RA−CCR7+, effector memory (TEM) CD45RA−CCR7− and CD45RA+ effectors (TEMRA) CD45RA+CCR7−. This last subset was mainly evident in CD8+ cells.

PPD- and RD1-peptide-specific CD4+ cell effector functional subsets were principally TCM in LTBI compared to TEM in ATB, for example fewer PPD-specific CD4+ only secreting cells were TCM in ATB compared with LTBI (p=0.005) (FIG. 2B). Comparisons of HIV-infected with uninfected patients were non-significant except for the CD4+RD1-peptide-specific IFN-γ-only- and TNF-α/IL-2-dual-secreting subsets, fewer of which were TCM in HIV-infected than uninfected subjects (p=0.030 and 0.006) (FIG. 6).

In contrast to the CD4+ effector functional subsets, CD4+ IL-2-only PPD- (FIG. 2B) and RD1-peptide-specific cells (data not shown) were principally TCM in both ATB and LTBI and were therefore unaffected by TB disease stage. CD8+ IFN-γ-only cellular responses to PPD and RD1-peptides were mostly TEM and TEMRA (data not shown).

CD127 (IL7Rα) expression is reduced following antigen stimulation in effector T-cells (Schluns et al. Nat Rev Immunol 2003; 3:269-79.) and defines CD4+ and CD8+ subsets of differentiated murine T effector cells distinct from effector memory cells (Kaech et al. Nat Immunol 2003; 4:1191-8; Harrington et al. Nature 2008; 452:356-60). We therefore measured CD127 expression on antigen-specific CD4+ functional T-cell subsets (FIG. 3A).

A smaller percentage of PPD- and RD1-peptide-specific CD4+ cells expressed CD127 in ATB compared with LTBI, for example a lower percentage of PPD-specific CD4+ IFN-γ-only- and TNF-α-only-secreting cells expressed CD127 in ATB compared with LTBI (p<0.001 and p=0.003 respectively) (FIG. 3B). Expression of CD127 on antigen-specific cells was unaffected by HIV status (FIG. 3B).

However, in patients with HIV co-infection, frequencies of several subsets of PPD-specific T-cells expressing CD127 correlated with CD4 count (FIG. 3C). Similarly, for RD-1-peptide-specific cells, IFN-γ/IL-2-dual-producing cells expressing CD127 correlated with CD4 count (Rho=0.647; p=0.047) and HIV VL correlated inversely with IFN-γ-only (Rho=−0.780; p=0.013) and IFN-γ/TNF-α-dual-secreting CD127− expressing cells (Rho=−0.727; p=0.005) (data not shown).

Example 3—Expansion of Differentiated CD4+ Functional Effector T-Cells in ATB Versus LTBI We next investigated the potential of combined phenotypic and functional measurement as a clinical biomarker. We determined the percentage of PPD- and RD1-peptide-specific CD4+ cells secreting IFN-γ-only or TNF-α-only that were differentiated effector cells (TEFF; CD45RA−CCR7−CD127−) (FIGS. 4A (ATB) and B (LTBI)).

In ATB, compared with LTBI, a higher percentage of CD4+ cells secreting IFN-γ-only or TNF-α-only in response to PPD and RD1-peptides were TEFF. This was most significant for CD4+ PPD-specific CD4+ cells secreting TNF-α-only (p<0.0001) and IFN-γ-only (p<0.0001). A cut off of >17.3% of TNF-α-only cells of TEFF phenotype distinguished ATB from LTBI with 100% sensitivity (95% CI 73.5-100.0) and 92.9% specificity (95% CI 66.1-99.8) (Table 2).

In ROC analysis, area under the curve was 0.99 (95% CI 0.97-1.01; p<0.0001) (FIG. 4C). Similar although slightly less discriminatory ROC curves were generated for PPD-specific IFN-γ-only cells and for RD-1-specific cells (FIG. 4C).

To test whether this approach was robust to differences in disease site we compared individuals with active pulmonary (PTB) and extra-pulmonary disease (EPTB). We found no significant difference in the proportion of PPD-specific cells secreting IFN-γ-only, or TNF-α-only that were TEFF (FIG. 4D) when stratified by site of disease or HIV co-infection. There was also no difference in the proportion of RD-1 peptide-specific cells that were TEFF when stratified by disease site (data not shown).

The operator conducting analyses (KMP) was also involved in participant recruitment and therefore not blinded to patient categorization. To demonstrate integrity and reproducibility of the results, data for all study participants was re-gated and re-analysed by a second independent operator (HSW) who was blinded to patient diagnoses.

Correlations between results obtained by operators 1 and 2 for the percentage of CD3+CD4+ cells secreting TNF-α-only (Rho=0.97, p<0.0001), the percentage of CD3+CD4+ TNF-α-only-secreting cells that are CD127+(Rho=0.96, p<0.0001) and the percentage of CD3+CD4+ TNF-α-only-secreting cells that are CD45RA−CCR7− (Rho=0.88, p<0.0001) were very strong. Using the 17.3% cut-off for TNF-α-only-secreting cells of TEFF phenotype to distinguish TB from LTBI, operator 2 misclassified 1 case of TB as LTBI, and 1 further case of LTBI as TB (data not shown).

TABLE 2

Clinical and radiological characteristics of cases sorted by percentage of TNF-α-only-secreting cells that were $T_{EFF}$ (CD45RA-CCR7-CD127-)

| No. | % $T_{EFF}$/ TNF-α only | HIV | CD4 | VL | Sputum smear | MTB culture | Culture site | Radiology (CXR or CT) | TB final diagnosis |
|---|---|---|---|---|---|---|---|---|---|
| S135 | 78.9 | + | 190 | 281671 | − | + | BAL and pleural fluid | Bilateral pleural effusions, lung and splenic nodules, peritoneal thickening | pulmonary |
| S126 | 75.0 | + | 69 | 601000 | + | + | Sputum | Azygos lobe focal consolidation in cavity, pleural effusions, no lymphadenopathy | pulmonary |

TABLE 2-continued

Clinical and radiological characteristics of cases sorted by percentage of TNF-α-only-secreting cells that were $T_{EFF}$ (CD45RA-CCR7-CD127-)

| No. | % $T_{EFF}$/ TNF-α only | HIV | CD4 | VL | Sputum smear | MTB culture | Culture site | Radiology (CXR or CT) | TB final diagnosis |
|---|---|---|---|---|---|---|---|---|---|
| S221 | 72.4 | − | na | na | nt | + | Lymph node | Enlarged low density lymph nodes in mediastinum and left axilla | extra pulmonary |
| S059 | 46.9 | + | 140 | <100 | + | + | Sputum and BAL | Effusion, thickened pleura, loss of volume left lung, ground glass change | pulmonary |
| S184 | 40.5 | − | na | na | nt | + | Lymph node | Multiple mediatstianal, coeliac axis lymph nodes with nodules in spleen and breast | extra pulmonary |
| S193 | 37.6 | + | 136 | 28958 | nt | + | Lymph node | Axillary, para-aortic and abdominal lymphadenopathy, subpleural nodules, liver lesions | extra pulmonary |
| S083 | 30.0 | − | na | na | − | + | Lymph node, BAL, peritoneal | Right pleural collection and right paratracheal lymphadenopathy | pulmonary |
| S076 | 29.2 | + | 200 | <50 | + | + | Left upper lobe, BAL, sputum | Consolidation and cavitation upper lobe, interstitial opacities, linear atelectasis | pulmonary |
| S115 | 28.6 | − | na | na | nt | + | Lymph node | Mediastianal lymphadenopathy | extra pulmonary |
| S146 | 20.1 | + | 250 | 52205 | nt | + | Lymph node | Supraclavicular, mediastinal and abdominal lymphadenopathy, nodular infiltrates | extra pulmonary |
| S195 | 18.0 | − | na | na | + | + | BAL and lymph node | Mediastinal, hilar and supraclavicular lymph nodes, patchy consolidation | pulmonary |
| S153 | 17.8 | − | na | na | nt | nt | nt | nil of note | LTBI |
| S082 | 17.5 | − | na | na | − | + | Lymph node | nil of note | extra pulmonary |
| S074 | 17.1 | − | na | na | − | *M fortuitum* | BAL | Opacification right upper lobe, small volume axillary and mediastinal lymph nodes | LTBI |
| S050 | 16.7 | + | 480 | 12479 | nt | nt | nt | nil of note | LTBI |
| S052 | 13.3 | + | 520 | 45719 | − | − | Sputum | nil of note | LTBI |
| S177 | 12.8 | − | na | na | nt | nt | nt | nil of note | LTBI |
| S094 | 10.9 | + | 660 | <50 | nt | nt | nt | Heavily calcified nodule and small lymph nodes right upper lobe | LTBI |
| S092 | 10.3 | nt | na | na | nt | nt | nt | nil of note | LTBI |
| S145 | 9.4 | − | na | na | nt | nt | nt | nt | LTBI |
| S098 | 8.6 | − | na | na | nt | nt | nt | (Fractured ribs T4-9 posteriorly) | LTBI |
| S047 | 8.5 | + | 360 | <50 | nt | nt | nt | nil of note | LTBI |
| S079 | 6.2 | nt | na | na | nt | nt | nt | nil of note | LTBI |
| S001 | 5.9 | + | 430 | 775 | nt | nt | nt | nil of note | LTBI |
| S099 | 5.8 | nt | na | na | nt | nt | nt | nil of note | LTBI |

TABLE 2-continued

Clinical and radiological characteristics of cases sorted by percentage of TNF-α-only-secreting cells that were $T_{EFF}$ (CD45RA-CCR7-CD127-)

| No. | % $T_{EFF}$/ TNF-α only | HIV | CD4 | VL | Sputum smear | MTB culture | Culture site | Radiology (CXR or CT) | TB final diagnosis |
|---|---|---|---|---|---|---|---|---|---|
| S120 | 4.7 | nt | na | na | nt | nt | nt | Fibrosis both apices, hilar lymphadenopathy, pleural thickening | LTBI |
| S097 | na | + | 177 | 19906 | + | − | Sputum | Subcarinal and axillary lymph nodes | pulmonary |
| S029 | na | + | 530 | <50 | nt | nt | nt | nil of note | LTBI |
| S025 | na | + | 330 | <50 | nt | nt | nt | nil of note | LTBI |
| S197 | na | + | 210 | <50 | nt | nt | nt | nil of note | LTBI |
| S201 | na | − | na | na | nt | nt | nt | nil of note | LTBI |
| S171 | na | + | 365 | <50 | nt | nt | nt | nil of note | LTBI |
| S191 | na | + | 530 | 13328 | nt | nt | nt | nt | LTBI |
| S121 | na | − | na | na | nt | nt | nt | nil of note | LTBI |

TB = tuberculosis,
LTBI = Latent TB infection,
Pos = positive,
Neg = negative,
nt = not tested,
na = not applicable,
BAL = bronchoalveolar lavage,
CXR = chest x-ray,
CT = computerised tomography.
Those above the top bold dividing line would be predicted to have ATB and those below it LTBI. Those below the second bold dividing line did not have a positive TNF-α-only response to PPD.

Example 4—Diagnosis of Infection with MTB

ELISpot platforms such that use MTB-specific antigens such as the T-SPOT®. TB are a highly sensitive and highly specific method to demonstrate the presence of infection with MTB (Dinnes, Deeks et al. 2007). The antigens utilised are either encoded by or associated with the region of difference 1 (RD1) including ESAT-6, CFP-10, Rv3879c, Rv3873 and Rv3615c which are both specific and immunodominant for MTB infection (Dosanjh, Hinks et al. 2008) (Dosanjh, Bakir et al. 2011). This approach is now recommended by health protection organisations worldwide for the diagnosis of LTBI. The ELISpot platform has the following advantages
   a) Standardisation of cell number in each well, this is a theoretical advantage in immunosuppression and data suggests that this test retains sensitivity when used in HIV co-infected individuals, unlike the TST (Chapman, Munkanta et al. 2002).
   b) Highly sensitive method of detection. This allows the use of several MTB-specific antigens, which can be used to distinguish MTB infection without confounding by prior BCG vaccination. Use of these antigens in the flow cytometry method of Example 5 is also possible, but responses can be too small to fully characterise. The most sensitive platform as the initial screening assay is therefore preferable to attain the highest diagnostic rate.

Method:
1. Take 5-10 mls peripheral blood from the patient into a TSpot. TB assay tube.
2. Separate out the peripheral blood mononuclear cells.
3. Place the counted cells into a 96-well TSpot. TB plate with negative control, positive control and test wells in duplicate.
4. Stimulate overnight with MTB-specific antigens.
5. Read on an AIDS ELISpot reader.
6. Stratify into positive and negative according to manufacturer's predefined threshold.

This method of diagnosing MTB infection may preferably then be followed by the method described in Example 5.

Example 5: Distinction of Active and Latent TB Infection and Indication of Mycobacterial Disease Activity Multi-parameter flow cytometry is a powerful tool for the interrogation of cellular immunity for measurement of responses to PPD, RD1, live or dead MTB and BCG. Simple flow cytometry procedures are used for monitoring in HIV infection (CD4 counts). Complex staining procedures are used for diagnostics of immune cancers such as leukaemia. There are currently no multi-colour flow cytometry assays for diagnostic use in the field of TB.

The test (which may preferably be performed as a second step after the test described in Example 4) measures a novel combination of cellular targets, not previously investigated simultaneously:
   1. Dead cell marker (allows removal of dead cells from analysis)
   2. Cluster of differentiation (CD) 3 fluorochrome-conjugated antibody (identifies T-cells)
   3. CD4 fluorochrome-conjugated antibody (identifies major T helper cell subset)
   4. C-C chemokine receptor 7 (CCR7) fluorochrome-conjugated antibody
   5. CD127 also known as interleukin-7 receptor alpha fluorochrome-conjugated antibody (this is particularly under-investigated in TB)
   6. Interferon-gamma (IFN-γ) fluorochrome-conjugated antibody
   7. Interleukin-2 (IL-2) fluorochrome-conjugated antibody 8. Tumour necrosis factor-alpha (TNF-α) fluorochrome-conjugated antibody
9. CD45RA fluorochrome-conjugated antibody (loss of this marker identifies experienced T-cell memory subset, this may be dispensable in the final assay)
10. CD8 fluorochrome-conjugated antibody (identifies major T-cytotoxic cell subset, this marker may be dispensable in the final assay)

This method quantifies the proportion of live CD3+CD4+ cells secreting TNF-α or IFN-γ that do not express CD45RA, CCR7 or CD127 (effector phenotype). This is to distinguish active from latent infection and stratify those at risk of progression to active TB. The higher the percentage of TNF-α-only secreting cells that have this effector phenotype, the higher the likelihood that a patient has active TB (higher threshold) or risk of progression to active TB (lower threshold). The combined measurement of these MTB-specific phenotype and function markers and test-specific approach to flow cytometry data analysis has not previously been described.

Method:
1. Take 30 mls whole blood from the patient with a positive response from the test described in Example 1. (This could be done simultaneously with the step 1 phlebotomy).
2. Separate PBMCs using Ficoll-Paque solution.
3. Take 3-5 million cells per well and leave unstimulated (negative control) or stimulate for 16 hours with mitogen (positive control) and purified protein derivative (PPD) in duplicate. After 2 hours add a golgi apparatus blocking compound e.g. Monensin.
4. Stain cells with a live cell marker then with a cocktail of cell surface marker fluorochrome-conjugated antibodies.
5. Fix and permeabilise cells and stain with a cocktail of intracellular cytokine fluorochrome-conjugated antibodies.
6. Acquire at least 1 million events per well on a flow cytometer
7. Analyse data using a gating strategy specific for this test with flow cytometry software package e.g. FlowJo, Treestarinc.

Discussion of Results of Examples 1-3

Our detailed interrogation of antigen-specific T-cell phenotype and function has delineated the association of TB disease stage with MTB-specific cellular immunity. ATB was associated with an increased frequency of mono- or dual-functional CD4+ and CD8+ MTB-specific T-cells that secrete IFN-γ and/or TNF-α making these subsets potential biomarkers of disease activity.

Simultaneous evaluation of memory phenotype of responding cells provided a more sensitive and specific surrogate than CD4+ functional profile alone. Expression of CD45RA, CCR7 and CD127 on MTB-specific T-cells secreting only IFN-γ or TNF-α was lowest in those with ATB. Memory phenotype was not exclusively linked to the functional profile (except for IL-2-only cells which were mainly $T_{CM}$) but was closely related to underlying TB stage. These markers might therefore serve as indicators of TB activation.

Combined measurement of both functional profile and differentiation phenotype provided a highly discriminatory immunological read-out for ATB and LTBI. In those with ATB, >17.3% of PPD-specific CD4+ TNF-α-only-secreting cells were CD45RA− CCR7−CD127− and this phenotype was therefore strongly associated with activated infection. Given that responses to PPD are less specific for MTB infection than responses to RD-1 antigens, this PPD-specific T cell signature may be used to distinguish TB from LTBI in the second step of a two-step diagnostic testing strategy, where MTB infection has been ruled-in at step one by a positive result in an RD-1-based immunodiagnostic test (e.g. IGRA).

Our data shows that the frequency of CD8+ MTB-specific cells, and therefore proportion of responders, was increased in ATB and this approach holds promise for the discrimination of TB disease stage especially in HIV co-infection where all participants had a positive response to MTB peptides. This association precludes the comparison of combined function and phenotype of MTB-specific CD8+ cells, however, because non-responders were by default mainly in the LTBI group. Measurement of CD8+ functional subsets in ATB and LTBI was therefore not sufficiently discriminatory for active and LTBI in our cohort.

In this study we included individuals with HIV co-infection to compare and distinguish the impact of ATB on MTB-specific cellular immunity with the impact of HIV co-infection. Where CD4+ MTB-specific effector-like cells were influenced by TB disease stage, the impact of HIV co-infection per se was rarely significantly associated with these changes. This may have been partially due to the inclusion of patients who were treated for HIV infection.

However, in the case of CD127, stratification by CD4 count showed that the stage of HIV disease influenced expression of this marker on MTB-specific T-cells. Reduced CD127 expression on HIV-specific CD8+ T-cells (reviewed in Crawley et al. Immunol Cell Biol 2011 Aug. 23. doi: 10.1038/icb.2011.66) and CD4+ T-cells (Dunham R M, et al. J Immunol 2008; 180:5582-92) is observed with HIV disease progression, but a relationship between HIV disease progression and CD127 expression on MTB-specific T-cells has not previously been noted. Our finding indicates that in HIV co-infection, MTB-antigen-specific CD4+ cells lose CD127 expression with advancing HIV disease and are therefore potentially more differentiated. This effect could be directly virus-induced or secondary to increasing subclinical mycobacterial burden with advancing HIV infection.

Our cohort included individuals with both pulmonary and extra-pulmonary infection. HIV infection is more commonly associated with TB dissemination as evidenced by the widespread involvement in some of these individuals. Despite some variation in clinical phenotype of those with ATB, our biomarker reliably distinguished TB stage, regardless of site of disease, suggesting that it may remain robust across the clinical TB disease spectrum and therefore have wide applicability. No individuals with LTBI developed ATB during 12 months of follow-up suggesting that, in our cohort (recruited in a TB non-endemic area), subclinical TB was not present in those classified as LTBI. The lack of continuous exogenous priming or re-stimulation due to TB exposure distinguishes our cohort from others recruited from TB endemic areas and removes this is as a possible confounding effect on the immunological changes we observed.

Through dissection of the impact of varying TB stage as a surrogate for mycobacterial pathogen burden, with and without HIV co-infection, we have identified cellular changes that are highly sensitive to TB activity.

Example 6: Inverse Correlation with Time Since Estimated Exposure to TB

In further work carried out amongst an entirely distinct cohort of HIV-uninfected individuals with latent TB infection (LTBI) (Table 3), the inventors have demonstrated that the immunological signature of the proportion of PPD-specific or ECR-specific TNF-α-only T cells that are CD45RA−CCR7−CD127−) inversely correlates with time since estimated exposure to TB (FIGS. 7 (a) and (b)).

"ECR" refers to the combination of ESAT-6 and CFP-10 and Rv3615c (otherwise known as EspC). Each of these are antigens that are strongly and widely recognised by T cells in MTB-infected people but not in BCG-vaccinated, MTB-uninfected people. Hence, unlike PPD, ECR is a MTB-specific cocktail of T cell antigens.

This second cohort includes recent (<6 months) contacts of known pulmonary TB cases and individuals from high TB incidence countries who have been in the UK for at least 2 years with no known TB exposure within that time ('remote' contacts). For remote contacts, time since entry to the UK was used as a proxy measure for time since TB exposure. Given the far higher risk of progression to TB disease within the first few years following MTB infection, and the decline in risk over time thereafter, the inventor's novel T cell signature can stratify individuals with LTBI by their likelihood of developing disease.

TABLE 3

Demographics of HIV-uninfected LTBI cohort.

| Patient ID | Age | Sex | TST (+/−) | IGRA (+/−) | Ethnicity | Time since TB exposure* |
|---|---|---|---|---|---|---|
| T1002 | 57 | M | + | + | Black Caribbean | 5 months |
| T1070 | 50 | M | + | + | White (British) | 2 months |
| T1204 | 21 | F | + | + | Bangladeshi | 1 month |
| T1208 | 24 | M | + | + | White (British) | 4 months |
| T1215 | 22 | M | + | + | White (British) | 4 months |
| T1263 | 41 | M | + | + | White (British) | 3 months |
| T496 | 33 | M | NT | + | White (Eastern European) | 6 months |
| T508 | 31 | F | + | + | White (Western European) | 2 months |
| T566 | 30 | M | + | + | Hispanic (South American) | 4 months |
| T846 | 43 | F | + | NT | Black Caribbean | Ongoing |
| T854 | 44 | M | + | + | White (British) | 3 months |
| T475 | 29 | M | NT | + | Indian | 3 months |
| T505 | 40 | F | + | + | Black African | 2 months |
| T752 | 41 | F | + | + | Asian (Other) | Ongoing |
| T845 | 33 | M | − | − | Black Africa | 3 months |
| T1044 | 35 | F | − | + | Black African | 2 years |
| T1169 | 53 | M | + | + | Middle Eastern (Other) | 28 years |
| T1224 | 25 | M | NT | + | Indian | 3 years |
| T1225 | 21 | F | NT | + | Chinese | 7 years |
| T1234 | 24 | F | NT | + | Indian | 3 years |
| T1235 | 24 | M | NT | + | Indian | 2 years |
| T1250 | 26 | F | NT | + | Indian | 3 years |
| T1265 | 25 | M | + | + | Indian | 3 years |
| T489 | 36 | F | + | + | Black Africa | 14 years |
| T491 | 34 | F | NT | + | Black African | 13 years |
| T515 | 37 | M | − | + | Asian (Other) | 2 years |
| T957 | 29 | F | + | + | Pakistani | 2 years |
| T1206 | 26 | M | − | + | Asian (other) | 2 years |

M: male;
F: female;
NT: not tested
*Estimated based on time since exposure to a known TB index case (for recent contacts) or time since emigration from a high TB incidence country (for remote contacts).

REFERENCES

Caccamo, N., G. Guggino, et al. (2009). "Analysis of Mycobacterium tuberculosis-specific CD8 T-cells in patients with active tuberculosis and in individuals with latent infection." PLoS One 4(5): e5528.

Casey, R., D. Blumenkrantz, et al. "Enumeration of functional T-cell subsets by fluorescence-immunospot defines signatures of pathogen burden in tuberculosis." PLoS One 5(12): e15619.

Chapman, A. L., M. Munkanta, et al. (2002). "Rapid detection of active and latent tuberculosis infection in HIV-positive individuals by enumeration of Mycobacterium tuberculosis-specific T cells." AIDS 16(17): 2285-2293.

Cobelens, F. G., S. M. Egwaga, et al. (2006). "Tuberculin skin testing in patients with HIV infection: Limited benefit of reduced cutoff values." Clinical Infectious Diseases 43(5): 634-639.

Diel, R., D. Goletti, et al. (2011). "Interferon-gamma release assays for the diagnosis of latent Mycobacterium tuberculosis infection: a systematic review and meta-analysis." Eur Respir J 37(1): 88-99.

Dinnes, J., J. Deeks, et al. (2007). "A systematic review of rapid diagnostic tests for the detection of tuberculosis infection." Health technology assessment 11(3): 1-196.

Dosanjh, D. P., M. Bakir, et al. (2011). "Novel M. tuberculosis antigen-specific T-cells are early markers of infection and disease progression." PLoS One 6(12): e28754.

Dosanjh, D. P., T. S. Hinks, et al. (2008). "Improved diagnostic evaluation of suspected tuberculosis." Ann Intern Med 148(5): 325-336.

Goletti, D., O. Butera, et al. (2006). "Region of difference 1 antigen-specific CD4+ memory T cells correlate with a favorable outcome of tuberculosis." J Infect Dis 194(7): 984-992.

Harari, A., S. Petitpierre, et al. (2004). "Skewed representation of functionally distinct populations of virus-specific CD4 T cells in HIV-1-infected subjects with progressive disease: changes after antiretroviral therapy." Blood 103(3): 966-972.

Harari, A., V. Rozot, et al. "Dominant TNF-alpha+ Mycobacterium tuberculosis-specific CD4+ T cell responses discriminate between latent infection and active disease." Nat Med 17(3): 372-376.

HPA. (2011). "Tuberculosis in the UK." Retrieved December 2011, from http://www.hpa.org.uk/webc/HPAweb-File/HPAweb_C/1317131791612.

Millington, K. A., J. A. Innes, et al. (2007). "Dynamic relationship between IFN-gamma and IL-2 profile of Mycobacterium tuberculosis-specific T cells and antigen load." J Immunol 178(8): 5217-5226.

Mueller, H., A. K. Detjen, et al. (2008). "Mycobacterium tuberculosis-specific CD4+, IFNgamma+, and TNFalpha+ multifunctional memory T cells coexpress GM-CSF." Cytokine 43(2): 143-148.

Wang, X., Z. Cao, et al. (2010). "Association of mycobacterial antigen-specific CD4(+) memory T cell subsets with outcome of pulmonary tuberculosis." The Journal of infection 60(2): 133-139.

WHO. (2011). "TB/HIV facts" Retrieved December 2011, 2011, from http://www.who.int/tb/challenges/hiv/factsheet_hivtb_2011.pdf.

Crawley, A. M. and Angel, J. B. "Expression of gamma-chain cytokine receptors on CD8(+) T cells in HIV infection with a focus on IL-7Ralpha (CD127)", Immunol Cell Biol, 2011 Aug. 23. doi: 10.1038/icb.2011.66

The invention claimed is:
1. A method of determining tuberculosis (TB) infection status in an individual comprising:
   (i) providing a sample comprising T-cells from said individual;
   (ii) exposing the sample of (i) to one or more TB antigens;

(iii) identifying T-cells in the sample that are CD4 positive and (a) secrete TNF-α without secreting IFN-γ; or (b) secrete IFN-γ without secreting TNF-α;

(iv) assessing the number of CD4+ T cells of (iii)(a) or (b) for CCR7 and CD127 expression; and (v) calculating the number of CD4+, CCR7− and CD127− cells identified in (iv) as a percentage of the CD4+ T cells identified in (iii)(a) or (b);

the higher the percentage of CD4+ cells that are CCR7− and CD127− calculated in step (v), the greater the likelihood that said individual has an active TB infection, and wherein steps (iii) and (iv) can be carried out either sequentially or simultaneously.

2. The method of claim 1 wherein the CD4+ T cells of (iii)(a) or (b) are additionally assessed for CD45RA expression in step (iv), and wherein in step (v) the CD4+, CCR7− and CD127− cells are CD4+, CCR7−, CD127− and CD45RA− cells.

3. The method of claim 1 wherein the cells identified in step (iii)(a) or (b) additionally do not secrete IL-2.

4. The method of claim 1 wherein the cells identified in step (iii)(a) or (b) are CD3 positive.

5. The method of claim 1 wherein the T-cells identified in step (iii)(a) or (b) are live T-cells.

6. The method of claim 1 wherein
i) the individual is infected with HIV and/or
ii) the individual has been infected with TB at any site and/or
iii) the sample is a blood sample, a PBMC sample, a bronochoalveolar lavage (BAL) sample or a cerebral spinal fluid (CSF) sample, and/or
iv) steps (iii) and/or (iv) are performed by multi-parameter flow cytometry.

7. The method of claim 1 further comprising first performing an assay to determine whether said individual is infected with TB.

8. A method of treating a subject infected with TB comprising:
(a) conducting the method of claim 1; and
(b) administrating treatment to subjects identified as having a TB infection.

9. A kit for determining tuberculosis (TB) infection status in an individual comprising:
(i) a composition comprising a plurality of antibodies or antigen-binding fragments thereof that binds to each of CD4, CCR7 and CD127 and wherein the plurality comprises antibodies or antigen-binding fragments thereof that are individually specific for each of CD4, CCR7 and CD127;
(ii) a composition comprising a plurality of antibodies or antigen-binding fragments thereof that binds to each of TNF-α and IFN-γ and wherein the plurality comprises antibodies or antigen-binding fragments thereof that are individually specific for each of TNF-α and IFN-γ; and
(iii) instructions for use wherein said kit optionally comprising one or more TB antigens, a live and/or dead cell discriminator, a positive control, and detectably labelled antibodies or antigen-binding fragments thereof that bind to one or more of CD3, CD45RA and/or IL-2.

10. The method of claim 5 wherein the T-cells identified in step (iii)(a) or (b) are identified as live T-cells by use of a dead cell marker.

11. The method of claim 7, wherein said assay is an ELISpot platform and/or an interferon gamma release assay (IGRA).

* * * * *